(12) United States Patent
Korenevski et al.

(10) Patent No.: US 10,172,946 B2
(45) Date of Patent: *Jan. 8, 2019

(54) MONODISPERSE GLYCOGEN AND PHYTOGLYCOGEN NANOPARTICLES AND USE THEREOF AS ADDITIVES IN COSMETICS, PHARMACEUTICALS, AND FOOD PRODUCTS

(71) Applicant: Mirexus Biotechnologies Inc., Guelph (CA)

(72) Inventors: Anton Korenevski, Guelph (CA); Erzsebet Papp-Szabo, Guelph (CA); John Robert Dutcher, Guelph (CA); Oleg Stukalov, Kitchener (CA)

(73) Assignee: MIREXUS BIOTECHNOLOGIES INC., Guelph (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/787,226

(22) PCT Filed: Apr. 25, 2014

(86) PCT No.: PCT/CA2014/000379
§ 371 (c)(1),
(2) Date: Oct. 26, 2015

(87) PCT Pub. No.: WO2014/172785
PCT Pub. Date: Oct. 30, 2014

(65) Prior Publication Data
US 2016/0083484 A1    Mar. 24, 2016

Related U.S. Application Data

(60) Provisional application No. 61/816,686, filed on Apr. 26, 2013.

(51) Int. Cl.
| | | |
|---|---|---|
| *A61K 47/36* | (2006.01) |
| *A61K 8/73* | (2006.01) |
| *C08L 5/00* | (2006.01) |
| *A61Q 17/04* | (2006.01) |
| *A61K 8/04* | (2006.01) |
| *C08B 37/00* | (2006.01) |
| *A61Q 5/06* | (2006.01) |
| *A61Q 15/00* | (2006.01) |
| *A61Q 19/00* | (2006.01) |
| *A61Q 19/10* | (2006.01) |
| *A61K 8/02* | (2006.01) |
| *A61K 9/16* | (2006.01) |
| *A23L 19/00* | (2016.01) |
| *A23L 33/10* | (2016.01) |
| *A61Q 17/00* | (2006.01) |

(52) U.S. Cl.
CPC .............. *A61K 47/36* (2013.01); *A23L 19/00* (2016.08); *A23L 33/10* (2016.08); *A61K 8/0241* (2013.01); *A61K 8/046* (2013.01); *A61K 8/73* (2013.01); *A61K 9/16* (2013.01); *A61Q 17/04* (2013.01); *A61Q 19/00* (2013.01); *C08B 37/0009* (2013.01); *C08L 5/00* (2013.01); *A23V 2002/00* (2013.01); *A61K 2800/10* (2013.01); *A61Q 5/06* (2013.01); *A61Q 15/00* (2013.01); *A61Q 17/005* (2013.01); *A61Q 19/002* (2013.01); *A61Q 19/10* (2013.01)

(58) Field of Classification Search
CPC .......... A61K 9/16; A61K 8/046; A61K 47/36; A61K 8/0241; A61K 2800/10; A61Q 17/04; A61Q 19/00; A61Q 5/06; A61Q 17/005; A61Q 19/002; A61Q 19/10; A61Q 15/00; C08L 5/00; C08B 37/0009; A23L 19/00; A23L 33/10; A23V 2002/00
USPC ................... 424/401, 499; 428/402; 435/97; 514/777; 536/123.1
See application file for complete search history.

(56) References Cited

U.S. PATENT DOCUMENTS

| | | |
|---|---|---|
| 2,189,854 A | 2/1940 | Brown et al. |
| 2,708,628 A | 5/1955 | Bauernfeind et al. |
| 4,803,075 A | 2/1989 | Wallace et al. |
| 5,093,109 A | 3/1992 | Mausner |
| 5,256,404 A | 10/1993 | Martino et al. |

(Continued)

FOREIGN PATENT DOCUMENTS

| | | |
|---|---|---|
| AU | 199934115 B2 | 10/1999 |
| CA | 2870967 A1 | 10/2013 |

(Continued)

OTHER PUBLICATIONS

Mirexus Biotechnology Inc, "Tiny Particles with Huge Possibility," Mar. 2009.*

(Continued)

*Primary Examiner* — Blessing M Fubara
(74) *Attorney, Agent, or Firm* — Norton Rose Fulbright Canada LLP

(57) ABSTRACT

Monodisperse glycogen or phytoglycogen nanoparticles are polyfunctional additives suitable for use in aqueous or alcohol-based cosmetic, pharmaceutical, or food formulations. The nanoparticles may be isolated from various sources (such as corn), and are optionally modified with a range of organic moieties (such as octenyl succinic acid). The monodisperse and particulate nature of the glycogen/phytoglycogen is believed to render such materials useful as rheological modifiers (including modulation of thixotropic behavior), stabilizers of organic and biological materials, and photostabilizers in sunscreens.

15 Claims, 7 Drawing Sheets

(56) References Cited

U.S. PATENT DOCUMENTS

| | | | |
|---|---|---|---|
| 5,552,135 | A | 9/1996 | Cioca et al. |
| 6,146,857 | A | 11/2000 | Pauly et al. |
| 6,165,450 | A | 12/2000 | Chaudhuri et al. |
| 6,451,362 | B1 | 9/2002 | Singh et al. |
| 6,486,139 | B1 | 11/2002 | Cavallo et al. |
| 7,108,860 | B2 | 9/2006 | Dueva et al. |
| 7,217,423 | B2 | 5/2007 | Golz-Berner et al. |
| 8,986,771 | B2 | 3/2015 | Yao |
| 2004/0052749 | A1* | 3/2004 | Golz-Berner ............ A61K 8/14 424/70.13 |
| 2009/0035234 | A1 | 2/2009 | Cunningham et al. |
| 2009/0253794 | A1 | 10/2009 | Tomono et al. |
| 2009/0281198 | A1 | 11/2009 | Muroyama et al. |
| 2010/0217373 | A1 | 10/2010 | Marchitto et al. |
| 2010/0272639 | A1* | 10/2010 | Dutcher ............ A61K 47/4823 424/1.37 |
| 2011/0269849 | A1 | 11/2011 | Yao |
| 2012/0220547 | A1 | 8/2012 | Russo et al. |
| 2013/0017308 | A1 | 1/2013 | Yao |
| 2014/0066363 | A1 | 3/2014 | Bhunia et al. |
| 2014/0303365 | A1 | 10/2014 | Zhang |
| 2015/0080220 | A1 | 3/2015 | Yao et al. |
| 2016/0068615 | A1 | 3/2016 | Russo et al. |

FOREIGN PATENT DOCUMENTS

| | | |
|---|---|---|
| CN | 104379175 A | 2/2015 |
| EP | 07082882 B1 | 12/2002 |
| EP | 0860448 B1 | 9/2004 |
| EP | 1813678 A1 | 8/2007 |
| EP | 2501468 A2 | 9/2012 |
| EP | 2838564 A1 | 2/2015 |
| JP | 6217-008505 A | 8/1987 |
| JP | S62178505 A | 8/1987 |
| JP | 63290809 A | 11/1988 |
| JP | H11255657 A | 9/1999 |
| JP | H11349603 A | 12/1999 |
| JP | 2000095660 A | 4/2000 |
| JP | 2000-247849 A | 9/2000 |
| JP | 2000247849 A | 9/2000 |
| JP | 200007707 A | 7/2001 |
| JP | 3204321 B2 | 9/2001 |
| JP | 2002-193740 A | 7/2002 |
| JP | 2002-523584 A | 7/2002 |
| JP | 2006-304701 A | 4/2005 |
| JP | 4762383 B2 | 8/2011 |
| JP | 2012062273 A | 3/2012 |
| JP | 2012153616 A | 8/2012 |
| JP | 2013-064134 A | 4/2013 |
| JP | 2015-519312 A | 7/2015 |
| JP | 2016023155 A | 2/2016 |
| JP | 2016-526053 A | 9/2016 |
| WO | WO 99/47120 * | 9/1999 |
| WO | 00/35490 A2 | 6/2000 |
| WO | 00/44232 A1 | 8/2000 |
| WO | 2004/022602 A1 | 3/2004 |
| WO | 2009/083561 A1 | 7/2009 |
| WO | 2009081287 A2 | 7/2009 |
| WO | 2009095341 A1 | 8/2009 |
| WO | 2011/062999 A2 | 5/2011 |
| WO | 2012006169 A2 | 1/2012 |
| WO | 2012/109121 A1 | 8/2012 |
| WO | 2012101473 A1 | 8/2012 |
| WO | 2013/019977 A2 | 2/2013 |
| WO | 2013/056227 A2 | 4/2013 |
| WO | 2013/135471 A1 | 9/2013 |
| WO | 2013/158992 A1 | 10/2013 |

OTHER PUBLICATIONS

Bi, L. et al (2011). Carbohydrate nanoparticle-mediated colloidal assembly for prolonged efficacy of bacteriocin against food pathogen. Biotechnology and Bioengineering, 108(7), 1529-1536.

Bi, L., Yang, L., Narsimhan, G., Bhunia, A. K., & Yao, Y. (2011). Designing carbohydrate nanoparticles for prolonged efficacy of antimicrobial peptide. Journal of Controlled Release, 150(2), 150-156.

Fermentas Certificate of Analysis Glycogen 2006.

Ikeda Corporation, Specification—Phytoglycogen, 2003.

Ikeda Corporation, Study on QPFC Phytoglycogen.

Life Technologies, Glycogen, 2004.

Powell PO, Sullivan MA, Sweedman MC, Stapleton DI, Hasjim J, Gilbert RG. Extraction, isolation and characterisation of phytoglycogen from su-1 maize leaves and grain. Carbohydr Polym. 2014, ;101:423-31.

Roche Diagnostics GmbH, Roche Applied Science, Glycogen From Mussels, Cat No. 10 901 393 001, 2014.

Sagiv, Assaf E. et al, "The connection between in vitro water uptake and in vivo skin moisturization", Skin Research and Technology 2003, vol. 9, pp. 306-311.

Scheffler SL, Huang L, Bi L, Yao Y. In vitro digestibility and emulsification properties of phytoglycogen octenyl succinate. J Agric Food Chem. 2010 58(8):5140-6.

Scheffler SL, Wang X, Huang L, San-Martin Gonzalez F, Yao Y. Phytoglycogen octenyl succinate, an amphiphilic carbohydrate nanoparticle, and epsilon-polylysine to improve lipid oxidative stability of emulsions. J Agric Food Chem. Jan. 13, 2010;58(1):660-7.

Scheffler, Siqi L. et al, "In Vitro Digestibility and Emulsification Properties of Phytoglycogen Octenyl Succinate", 2010, J. Agric. Food Chem, vol. 58, pp. 5140-5146.

Aasen et al., 2015. A novel nanoprobe for multimodal imaging is effectively incorporated into human melanoma metastatic cell lines. Int. J. Mol. Sci. 16: 21658-21680.

Wondraczek, Holger et al, "Photoactive polysaccharides", Carbohydrate Polymers, 2011, vol. 83, pp. 1048-1061.

Liang et al., 2014. An efficient nonviral gene-delivery vector based on hyperbranched cationic glycogen derivatives, International Journal of Nanomedicine, 9: 419-435.

Huang, L et al (2011). Particulate structure of phytoglycogen nanoparticles probed using amyloglucosidase. Carbohydrate Polymers 83, 1665-1671.

Nakano, A et al (1997). Dispersion stability of phytoglycogen in water/phytoglycogen/various nonionic sufactant systems: effect of hydrophile-lipophile balance (HLB) of nonionic surfactants 70 (12), 2943-2949.

Somasundaran, P., Mehta, S., Rhein, L., & Chakraborty, S. (2007). Nanotechnology and Related Safety Issues for Delivery of Active Ingredients in Cosmetics. MRS Bulletin,32 (10), 779-786.

Mihranyan, A.; Ferraz, N.; Strømme, M. (2012).Current status and future prospects of nanotechnology in cosmetics. Prog. Mater. Sci. 57, 875-910.

Pignitter M., B. Dumhart, S. Gartner, F. Jirsa, G. Steiger, K. Kraemer, and V. Somoza. (2014) Vitamin A is Rapidly Degraded in Retinyl Palmitate-Fortified Soybean Oil Stored under Household Conditions Journal of Agricultural and Food Chemistry, 62 (30), 7559-7566.

Gaspar L. R, Maia Campos P. M. (2006). Evaluation of the photostability of different UV filter combinations in a sunscreen. Int J Pharm. 307(2):123-8.

Scalia S., Molinari A., Casolari A., Maldotti A. (2004) Complexation of the sunscreen agent, phenylbenzimidazole sulphonic acid with cyclodextrins: effect on stability and photo-induced free radical formation.Eur J Pharm Sci. 22(4):241-9.

Müller, B. and Van de Voorde, M. (2017) Nanomedicine in Dermatology: Nanotechnology in Prevention, Diagnosis, and Therapy, in Nanoscience and Nanotechnology for Human Health, Wiley-VCH Verlag GmbH & Co. KGaA, Neinheim, Germany.

Kockler J., M. Oelgemöller, S. Robertson, B. D. Glass. (2012). Photostability of sunscreens. Review. Journal of Photochemistry and Photobiology C: Photochemistry Reviews, 13 (1) 91-110.

Hajime Hiramatsu et al, "Function and application of corn phytoglycogen for cosmetics", Fragrance Journal, 1998, vol. 26, No. 3, pp. 49-54.

Machine Translated Version of Hajime Hiramatsu et al, "Function and application of corn phytoglycogen for cosmetics", Fragrance Journal, 1998, vol. 26, No. 3, pp. 49-54.

(56) References Cited

OTHER PUBLICATIONS

Machine Translated Version of JP 2002-193740 A.
Machine Translated Version of JP 2002-523584 A.
Machine Translated Version of JP 2016-526053 A.
Machine Translated Version of JP 2013-064134 A.

* cited by examiner

MONODISPERSE GLYCOGEN AND PHYTOGLYCOGEN NANOPARTICLES AND USE THEREOF AS ADDITIVES IN COSMETICS, PHARMACEUTICALS, AND FOOD PRODUCTS

CROSS-REFERENCE TO RELATED APPLICATIONS

This application claims priority from U.S. patent application 61/816,686 filed on Apr. 26, 2013 and its contents is incorporated herewith in its entirety.

TECHNICAL FIELD

This invention relates to use of glycogen and phytoglycogen as an additive.

BACKGROUND OF THE ART

Glycogen is a short-term energy storage material in animals. In mammals, glycogen occurs in muscle and liver tissues. It is comprised of 1,4-glucan chains, highly branched via α-1,6-glucosidic linkages with a molecular weight of $10^6$-$10^8$ Daltons. Glycogen is present in animal tissue in the form of dense particles with diameters of 20-200 nm. Glycogen is also found to accumulate in microorganisms, e.g., in bacteria and yeasts.

Phytoglycogen is a polysaccharide that is very similar to glycogen, both in terms of its structure and physical properties. It is distinguished from glycogen based on its plant-based sources of origin. The most prominent sources of phytoglycogen are kernels of sweet corn, as well as specific varieties of rice, barley, and sorghum.

Methods of producing glycogen and phytoglycogen from different sources are known in the art.

Various methods have been developed to isolate glycogen and phytoglycogen from living organisms.

Known methods include extraction from animal tissues, particularly from marine animals, especially mollusks, because of their ability to accumulate glycogen. See for example, methods described in U.S. Pat. Nos. 5,734,045, 5,597,913; Japanese patent application JP2006304701; Malcolm, J. The Composition of some New Zealand Foodstuffs. *Trans Proc R Soc N Z.* 1911 44:265-269; Ward J F et al. Extractions of Glycogen from Soft Shell Clams (*Mya arenaria*). *Chesapeake Sci.* 1966, 7(4):213-214; Wary C et al. 1H NMR spectroscopy study of the dynamic properties of glycogen in solution by steady-state magnetisation measurement with off-resonance irradiation. *Carbohydr Res.* 1998, 306(4):479-91; Matsui M, et al. Fine structural features of oyster glycogen: Mode of multiple branching. *Carbohydrate Polymers,* 1996, 31(4): 227-235; Sullivan M A et al. Improving size-exclusion chromatography separation for glycogen. *Journal of Chromatography A,* 2014. In press; the disclosures of which are incorporated by reference in their entirety.

Glycogen can also be extracted from mammals and, in particular from liver or muscle tissue, according to various methods see e.g. Popovski S. et al. The mechanism of aggregation of β-particles into α-particles in rat liver glycogen. *Biochemical Society Transactions* (2000) 28, Part 5, A336; Sullivan M A et al. Nature of alpha and beta particles in glycogen using molecular size distributions. *Biomacromolecules.* 2010 Apr. 12; 11(4):1094-100; Wanson J C & Drochmans P. Rabbit skeletal muscle glycogen. A morphological and biochemical study of glycogen beta-particles isolated by the precipitation-centrifugation method. *J Cell Biol.* 1968. 38(1):130-50; Somogyi, M. The solubility and preparation of phosphorus- and nitrogen-free glycogen. *J. Biol. Chem.* 1934.104: 245; Geddes R et al. The molecular size and shape of liver glycogen. *Biochem. J.* 1977. 163: 201-209; Devos P et al. The alpha particulate liver glycogen. A morphometric approach to the kinetics of its synthesis and degradation. *Biochem. J.* 1983, 209:159-165; Orrell S A & Bueding E. A Comparison of products obtained by various procedures used for the extraction of glycogen. *J Biol Chem.* 1964, 239:4021-4026; Bröjer J T et al. Effect of extraction time and acid concentration on the separation of proglycogen and macroglycogen in horse muscle samples. *Can J Vet Res.* 2002, 66(3):201-6; Bell D G & F G Young. Observations on the chemistry of liver glycogen. *Biochem. J.* 1934, 28:882-0; Stetten M R et al. A comparison of the glycogens isolated by acid and alkaline procedures. *J Biol Chem.* 1958, 232(1):475-488; Wary C et al. 1H NMR spectroscopy study of the dynamic properties of glycogen in solution by steady-state magnetisation measurement with off-resonance irradiation. *Carbohydr Res.* 1998, 306(4):479-91; Laskov R. & E. Margoliash. Properties of high molecular weight glycogen from rat liver. 1963. *Bull. Res. Counc. Isr.* 11: 351-362; Haverstick D M & Gold A H. Isolation of a polydisperse high-molecular-weight glycogen from rat liver. *Anal Biochem.* 1981 February; 111(1):137-45; Parker G J et al. AMP-activated protein kinase does not associate with glycogen alpha-particles from rat liver. *Biochem Biophys Res Commun.* 2007, 362(4):811-5; Sullivan M A et al. Improving size-exclusion chromatography separation for glycogen. *Journal of Chromatography A,* 2014. In press; the contents of each of which are incorporated by reference in their entirety.

Phytoglycogen can also be isolated from plant material according to various methods. See, for example, U.S. Pat. No. 5,895,686 and European patent EP0860448B1, and Wong, K S et al. Structures and properties of amylopectin and phytoglycogen in the endosperm of sugary-1 mutants of rice. *J. Cereal Sci.* (2003) 37: 139-149; Fujita N et al. Antisense inhibition of isoamylase alters the structure of amylopectin and the physicochemical properties of starch in rice endosperm. *Plant Cell Physiol* 2003, 44 (6): 607-618; which describe processes of isolating phytoglycogen from kernels of rice Verhoeven, T. et al. Isolation and characterisation of novel starch mutants of oats. *Journal of Cereal Science,* 2004, 40 (1): 69-79, which describes the isolation of phytoglycogen from oats; Burton R A et al. Starch granule initiation and growth are altered in barley mutants that lack isoamylase activity. *Plant J.* 2002, 31(1):97-112, which describes the isolation of phytoglycogen from barley; International patent application publication no. WO 2013/019977; U.S. Pat. No. 6,451,362; Rolland-Sabaté A., et al. Elongation and insolubilisation of alpha-glucans by the action of *Neisseria* polysaccharea amylosucrase. *J Cereal Sci.* 2004, 40:17-30; Dinges J R, et al. Molecular structure of three mutations at the maize sugary1 locus and their allele-specific phenotypic effects. *Plant Physiol.* 2001, 125 (3):1406-18; Morris D L & CT Morris. Glycogen in sweet corn. *Science.* 1939, 90(2332):238-239; Miao M, et al. Structure and digestibility of endosperm water-soluble α-glucans from different sugary maize mutants. Food Chem. 2014, 143:156-62; Miao M, et al. Structure and physicochemical properties of octenyl succinic esters of sugary maize soluble starch and waxy maize starch. *Food Chem.* 2014, 151:154-60; Powell P O, et al. Extraction, isolation and characterisation of phytoglycogen from su-1 maize leaves and grain. *Carbohydr Polym.* 2014, 101:423-31; Sullivan M A, et al. Improving size-exclusion chromatography separation for glycogen. *Journal of Chromatography A*, 2014. In press; Scheffler S L, et al. Phytoglycogen octenyl succinate, an amphiphilic carbohydrate nanoparticle, and epsilon-polylysine to improve lipid oxidative stability of emulsions. *J Agric Food Chem.* 2010 Jan. 13; 58(1):660-7; Scheffler S L, et al. In vitro digestibility and emulsification properties of phytoglycogen octenyl succinate. *J Agric Food Chem.* 2010 58(8):5140-6; and Huang, L., & Yao, Y. Particulate structure of phytoglycogen nanoparticles probed using amyloglucosidase. *Carbohydrate Polymers*, 2011, 83:1165-1171; which describe processes of isolating phytoglycogen from sweet corn; the disclosures of all of which are incorporated by reference in their entirety.

Glycogen can also be obtained from yeasts according to various methods as described, for example, in international patent application WO/1997/021828; U.S. Pat. No. 6,146,857; and Northcote D. The molecular structure and shape of yeast glycogen. *Biochem J.* 1953, 53(3): 348-352; the disclosures of which are incorporated by reference in their entirety.

Glycogen can also be obtained from bacteria according to various methods, as described, for example, in Levine S, et al. Glycogen of enteric bacteria. *J Bacteriol.* 1953, 66(6): 664-670; Sigal N, et al. Glycogen accumulation by wild-type and uridine diphosphate glucose pyrophosphorylase-negative strains of *escherichia coli*. *Arch Biochem Biophys.* 1964, 108:440-451; Chargaff E. & H. Moore. On bacterial glycogen: the isolation from avian tubercle bacilli of a polyglucosan of very high particle weight. *J. Biol. Chem.* 1944, 155: 493-501; Yoo S H, et al. Characterization of cyanobacterial glycogen isolated from the wild type and from a mutant lacking of branching enzyme. *Carbohydr Res.* 2002, 337(21-23):2195-203; Schneegurt M A, et al. Composition of the carbohydrate granules of the cyanobacterium, *Cyanothece* sp. strain ATCC 51142. *Arch Microbiol.* 1997, 167(2-3):89-98; and Schneegurt M A, et al. Oscillating behavior of carbohydrate granule formation and dinitrogen fixation in the cyanobacterium *Cyanothece* sp. strain ATCC 51142. *Bacteriol.* 1994, 176(6): 1586-1597; the contents of which are incorporated herein by reference in their entirety.

Glycogen and phytoglycogen may also be prepared using biosynthetic methods. U.S. Pat. No. 7,670,812 describes a process for the biosynthetic production of glycogen-like polysaccharides by exposing a mixture of enzymes to low molecular weight dextrins.

Glycogen and phytoglycogen may also be obtained from commercial sources. E.g. phytoglycogen derived from corn is sold commercially by IKEDA CORPORATION, Japan and KEWPIE CORPORATION, Japan; enzymatically synthesized glycogen is sold commercially under the name of BIOGLYCOGEN by Ezaki Glico Co.; LABORATOIRES SÉROBIOLOGIQUES S.A. (FRANCE) sells a glycogen derived from marine sources under the name DERMOSACCHARIDES® GY. Glycogen is also sold as a co-precipitant for the precipitation of nucleic acids and is offered commercially by many companies, such as Roche, Sigma-Aldrich, SERVA Electrophoresis GmbH, and Life Technologies.

Applications of glycogen, phytoglycogen and related glycogen-like material have been suggested.

U.S. Pat. No. 6,451,362 describes the use of phytoglycogen derived from sweet corn as a coating layer for ready-to-eat cereals, which slows down wetting of the cereal flakes and prolongs crunchiness. International patent application WO/2011/062999A2 describes the use of chemically modified phytoglycogen as an emulsification aid for food applications. United States patent application publication no. 201110269849A1 describes the use of chemically modified phytoglycogen to improve oxidative stability of lipids in food applications.

Japanese patent application JP1999000044901 proposes the use of phytoglycogen as an additive for hair formulations that imparts improved combing properties and shiny appearance to hair. U.S. Pat. No. 6,224,889 provides a skincare cosmetic composition that includes glycogen as one of several components suitable for protecting human skin from the effects of cold. United States patent application publication no. 2010/0273736 provides cosmetic formulations containing glycogen as the active ingredient for a skin softening/smoothing effect and U.S. Pat. No. 5,093,109 describes glycogen as an anti-aging agent that can be used for those purposes in cosmetic formulations. Japanese patent application JP-A-62-178 505 describes the use of glycogen as an emollient and hydrating agent in cosmetic formulations. United States patent application publication no. 2004-0052749 describes an aqueous gel for the skin comprising creatinine or a creatinine derivative, glycogen and phopholipid, which is claimed to have a revitalizing effect and to provide UV protection.

U.S. Pat. No. 4,803,075 discloses glycogen (along with maltose) as a biocompatible fluid lubricant that improves the intrudability of injectable implant biomaterials.

There is a growing need for incorporation of natural, non-toxic and biodegradable materials in food, personal care, paints, coating and other industrial products to replace petroleum-based chemicals. Polyfunctional additives in particular are in high demand since reducing the number of ingredients makes the formulation process easier and lowers the formulation cost. Further, in the personal care industry, ingredients that can be provided in concentrated liquid form are highly desirable since it simplifies the formulation process and enables easy handling by automatic dispensers and metering pumps.

BRIEF SUMMARY

In one embodiment, there is described a method for changing the rheological behavior of a water-based or alcohol-based formulation comprising adding a composition of monodisperse glycogen or phytoglycogen nanoparticles to the formulation.

In one embodiment, the formulation is thixotropic and the change in rheological behavior comprises an increase in rebuilding time. In one embodiment, the change in rheological behavior comprises imparting thixotropic behavior.

In one embodiment, the formulation is a dispersion or solution of at least one small molecule, polymer, biopolymer, colloidal particle or an oil.

In one embodiment, the formulation is a water-based formulation.

In one embodiment, the formulation is an alcohol-based formulation. In one embodiment, the alcohol is ethyl alcohol, propyl alcohol, isopropyl alcohol, ethylene glycol, propylene glycol, butylene glycol, dipropylene glycol, ethoxydiglycol, glycerol or a combination thereof.

In one embodiment, the composition has a polydispersity index of less than about 0.3 as measured by dynamic light scattering.

In one embodiment, at least 80% by dry weight of the composition is monodisperse glycogen or phytoglycogen nanoparticles having an average particle diameter of between about 30 nm and about 150 nm.

In one embodiment, the monodisperse glycogen or phytoglycogen nanoparticles are chemically modified. In one embodiment, the monodisperse glycogen or phytoglycogen nanoparticles are modified by chemical functionalization of at least one of its hydroxyl groups with a carbonyl group, an amine group, a thiol group, a carboxylic group, or a hydrocarbyl. In one embodiment, the hydrocarbyl group is an alkyl, vinyl or allyl group. In one embodiment, the monodisperse glycogen or phytoglycogen nanoparticle is modified with octenyl succinic acid.

In one embodiment, the composition comprises a natural gum.

In one embodiment, the composition is a food, a cosmetic, a personal care product, a nutraceutical, a pharmaceutical, a lotion, a gel, a paint, a coating, an ink, a lubricant, an excipient, a surface film, a stabilizer or a drilling mud.

In one embodiment, there is described a polyfunctional additive for water-based or alcohol-based formulations comprising monodisperse glycogen or phytoglycogen nanoparticles.

In one embodiment, the additive has a polydispersity index of less than about 0.3 as measured by dynamic light scattering. In one embodiment, the additive has a polydispersity index of less than about 0.2 as measured by dynamic light scattering. In one embodiment, the additive has a polydispersity index of less than about 0.1 as measured by dynamic light scattering.

In one embodiment, at least about 90% by dry weight of the additive is monodisperse glycogen or phytoglycogen nanoparticles having an average particle diameter of between about 30 nm and about 150 nm.

In one embodiment, about 90% by dry weight of the additive is phytoglycogen nanoparticles having an average particle diameter of between about 30 nm and about 150 nm.

In one embodiment, about 90% by dry weight of the additive is nanoparticles having an average particle diameter of between about 60 nm and about 110 nm.

In one embodiment, about 90% by dry weight of the additive is glycogen nanoparticles having an average diameter of between about 20 and about 60 nm.

In one embodiment, the monodisperse glycogen or phytoglycogen nanoparticles are chemically modified. In one embodiment, the monodisperse glycogen or phytoglycogen nanoparticles are modified by chemical functionalization of at least one of its hydroxyl groups with a carbonyl group, an amine group, a thiol group, a carboxylic group, or a hydrocarbyl. In one embodiment, the hydrocarbyl group is an alkyl, vinyl or allyl group. In one embodiment, the monodisperse glycogen or phytoglycogen nanoparticle is modified with octenyl succinic acid.

In one embodiment, the polyfunctional additive is in the form of a powder.

In one embodiment, the polyfunctional additive is in the form of a liquid.

In one embodiment, the polyfunctional additive is in the form of a gel.

In one embodiment, there is described a composition comprising a polyfunctional additive of the present invention and a water-based or alcohol-based formulation.

In one embodiment, the water-based or alcohol-based formulation is a solution or dispersion of at least one small molecule, polymer, biopolymer, colloidal particle or an oil.

In one embodiment, the composition is a water-based formulation.

In one embodiment, the composition is an alcohol-based formulation. In one embodiment, the alcohol is ethyl alcohol, propyl alcohol, isopropyl alcohol, ethylene glycol, propylene glycol, butylene glycol, dipropylene glycol, ethoxydiglycol, glycerol or a combination thereof.

In one embodiment, the polyfunctional additive comprises about 5 to about 25% w/w of the composition.

In one embodiment, the composition has thixotropic behaviour compared to the same composition without the polyfunctional additive.

In one embodiment, the composition is thixotropic and has increased rebuilding time compared to the same composition without the polyfunctional additive.

In one embodiment, the composition comprises a natural gum.

In one embodiment, the composition is a food, a cosmetic, a personal care product, a nutraceutical, a pharmaceutical, a lotion, a gel, a paint, a coating, an ink, a lubricant, an excipient, a surface film, a stabilizer or a drilling mud.

In one embodiment, the composition has improved solubility and stability compared to the same composition without the polyfunctional additive.

In one embodiment, the composition is a spray on personal care product.

In one embodiment, the spray on personal care product is a spray on cosmetic, a spray on sunscreen, a hairspray, a spray on deodorant, a spray on antiperspirant, a spray on aftershave or a spray on hand sanitizer.

Also described is a method for stabilizing a water-based or alcohol-based formulation comprising adding monodisperse glycogen or phytoglycogen nanoparticles to the formulation.

Also described is a method of imparting thixotropic behaviour to a water-based or alcohol-based formulation comprising adding monodisperse glycogen or phytoglycogen nanoparticles to the formulation.

Also described is a method of increasing rebuilding time in a thixotropic water-based or alcohol-based formulation comprising adding monodisperse glycogen or phytoglycogen nanoparticles to the formulation.

Also described is a method of increasing the photostability of organic compounds in a water-based or alcohol-based formulation comprising adding monodisperse glycogen or phytoglycogen nanoparticles to the formulation.

Also described is a method of protecting the bioactivity of a bioactive agent comprising admixing the bioactive agent with a composition of monodisperse glycogen or phytoglycogen nanoparticles.

DETAILED DESCRIPTION

Figure 1:
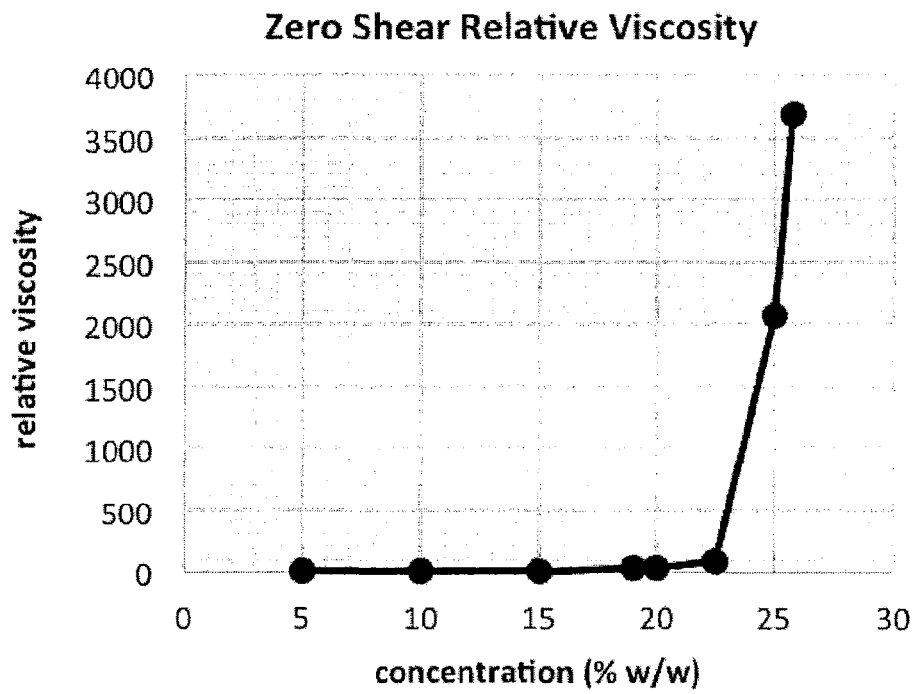
FIG. 1 shows the viscosity of monodisperse phytoglycogen nanoparticles in water at different concentrations.

In one embodiment, there is described a polyfunctional additive for water-based or alcohol-based formulations comprising glycogen or phytoglycogen. In one embodiment, the polyfunctional additive is monodisperse nanoparticles of glycogen or phytoglycogen.

In the present application glycogen and phytoglycogen include both glycogen and phytoglycogen derived from natural sources and synthetic glycogen and phytoglycogen.

Glycogen and phytoglycogen are molecules of α-D glucose chains having an average chain length of 11-12, with 1-4 linkage and branching point occurring at and with a branching degree of about 6% to about 13%.

Water-based formulations of the present invention include, in particular, dispersions, including emulsions and suspensions, and solutions of one or more of small molecules, polymers, biopolymers, colloidal particles and oils.

Alcohol-based formulations of the present invention include, in particular, dispersions, including emulsions and suspensions, and solutions of one or more of small molecules, polymers, biopolymers, colloidal particles and oils in one or more alcohols. In one embodiment, the alcohols are not restricted. In one embodiment, the alcohols are selected from ethyl alcohol, propyl alcohol, isopropyl alcohol, ethylene glycol, propylene glycol, butylene glycol, dipropylene glycol, ethoxydiglycol, glycerol and mixtures thereof.

While in one embodiment, glycogen and phytoglycogen used in novel methods described herein can be obtained using any known method or be obtained from a commercial source, the commercial products and yields of methods described above are highly polydisperse products that include both glycogen or phytoglycogen particles, as well as other products and degradation products of glycogen or phytoglycogen and do not exhibit inter alia the rheological properties of monodisperse compositions of glycogen and phytoglycogen. As detailed below, the present inventors have developed methods for producing monodisperse compositions of glycogen and phytoglycogen nanoparticles. The monodisperse and particulate nature of the compositions of the inventors are associated with properties that render them highly suitable for use as a polyfunctional additive.

Accordingly, in a preferred embodiment, monodisperse compositions of glycogen or phytoglycogen nanoparticles are used.

In one embodiment, polyfunctional additives as described herein may suitably be used in formulations in a concentration of up to about 25% w/w, between about 5 and about 25% w/w, between about 5 and about 20% w/w, between about 5 and about 15% w/w, between about 5 and about 10% w/w, between about 10 and about 25% w/w, between about 10 and about 20% w/w, between about 10 and about 15% w/w. In applications where a high viscosity is desirable, the polyfunctional additive may be used in formulations in concentrations above about 25% w/w. In applications where a gel or semi-solid is desirable, concentrations up to about 35% w/w can be used.

The polyfunctional glycogen or phytoglycogen additive is non-toxic, has no known allergenicity, and can be degraded by glycogenolytic enzymes (e.g. amylases and phosphorylases) of the human body. The products of enzymatic degradation are non-toxic, neutral molecules of glucose.

The polyfunctional additive is compatible with most personal care formulation ingredients such as emulsifiers, surfactants, thickeners, preservatives, and physical and chemical sunscreen active ingredients.

As detailed below, the polyfunctional additive is photostable and is also stable over a wide range of pH, electrolytes, e.g. salt concentrations.

United States patent application publication no. United States 20100272639 A1, assigned to the owner of the present invention and the disclosure of which is incorporated by reference in its entirety, provides a process for the isolation of glycogen from bacterial and shell fish biomass. The processes disclosed generally include the steps of cell disintegration by French pressing, or by chemical treatment; separation of insoluble cell components by centrifugation; elimination of proteins and nucleic acids from cell lyzate by enzymatic treatment followed by dialysis which produces an extract containing crude polysaccharides and lypopolysaccharides (LPS) or, alternatively, phenol-water extraction; elimination of LPS by weak acid hydrolysis, or by treatment with salts of multivalent cations, which results in the precipitation of insoluble LPS products; and purification of the glycogen enriched fraction by ultrafiltration and/or size exclusion chromatography; and precipitation of glycogen with a suitable organic solvent or a concentrated glycogen solution can be obtained by ultrafiltration or by ultracentrifugation; and freeze drying to produce a powder of glycogen. Glycogen isolated from bacterial biomass was characterized by MWt 5.3-12.7×10$^6$ Da, had particle size 35-40 nm in diameter and was monodisperse.

Methods of producing monodisperse compositions of phytoglycogen are disclosed in the International patent application entitled "Phytoglycogen Nanoparticles and Methods of Manufacture Thereof", which is being filed concurrently herewith and the disclosure of which is incorporated by reference in its entirety. In one embodiment, the described methods of producing monodisperse phytoglycogen nanoparticles include: a. immersing disintegrated phytoglycogen-containing plant material in water at a temperature between about 0 and about 50° C.; b. subjecting the product of step (a.) to a solid-liquid separation to obtain an aqueous extract; c. passing the aqueous extract of step (b.) through a microfiltration material having a maximum average pore size of between about 0.05 μm and about 0.15 μm; and d. subjecting the filtrate from step c. to ultrafiltration to remove impurities having a molecular weight of less than about 300 kDa, in one embodiment, less than about 500 kDa, to obtain an aqueous composition comprising monodisperse phytoglycogen nanoparticles. In one embodiment of the method, the phytoglycogen-containing plant material is a cereal selected from corn, rice, barley, sorghum or a mixture thereof. In one embodiment, step c. comprises passing the aqueous extract of step (b.) through (c.1) a first microfiltration material having a maximum average pore size between about 10 µm and about 40 µm; (c.2) a second microfiltration material having a maximum average pore size between about 0.5 µm and about 2.0 µm, and (c.3) a third microfiltration material having a maximum average pore size between about 0.05 and 0.15 µm. The method can further include a step (e.) of subjecting the aqueous composition comprising monodisperse phytoglycogen nanoparticles to enzymatic treatment using amylosucrose, glycosyltransferase, branching enzymes or any combination thereof. The method avoids the use of chemical, enzymatic or thermo treatments that degrade the phytoglycogen material. The aqueous composition can further be dried.

The polydispersity index (PDI) of a composition of nanoparticles can be determined by the dynamic light scattering (DLS) technique and, in this embodiment, PDI is determined as the square of the ratio of standard deviation to mean diameter (PDI=$(\sigma/d)^2$. PDI can also be expressed through the distribution of the molecular weight of polymer and, in this embodiment, is defined as the ration of $M_w$ to $M_n$, where $M_w$ is the weight-average molar mass and $M_n$ is the number-average molar mass (hereafter this PDI measurement is referred to as PDI*). In the first case, a monodisperse material would have a PDI of zero (0.0) and in the second case the PDI* would be 1.0.

In one embodiment, the polyfunctional additive comprises, consists essentially of, or consists of a composition of monodisperse glycogen or phytoglycogen nanoparticles. In one embodiment, the polyfunctional additive comprises, consists essentially of, or consists of a composition of monodisperse glycogen or phytoglycogen nanoparticles having a PDI of less than about 0.3, less than about 0.2, less than about 0.15, less than about 0.10, or less than 0.05 as measured by dynamic light scattering. In one embodiment, the polyfunctional additive comprises, consists essentially of, or consists of a composition of monodisperse glycogen or phytoglycogen nanoparticles having a PDI* of less than about 1.3, less than about 1.2, less than about 1.15, less than about 1.10, or less than 1.05 as measured by SEC MALS In one embodiment, the polyfunctional additive comprises, consists essentially of, or consists of a composition of monodisperse glycogen or phytoglycogen nanoparticles having an average particle diameter of between about 30 nm and about 150 nm. In one embodiment, the polyfunctional additive comprises, consists essentially of, or consists of a composition of monodisperse glycogen or phytoglycogen nanoparticles having an average particle diameter of about 60 nm to about 110 nm.

Due to its origin, monodisperse phytoglycogen nanoparticles are suitable for use in natural, vegan and organic formulations.

The methods of producing phytoglycogen nanoparticles as detailed in Example 1 and as taught in the international patent application entitled "Phytoglycogen Nanoparticles and Methods of Manufacture Thereof", which is being filed concurrently herewith, are amenable to preparation under food grade conditions.

In one embodiment, the glycogen or phytoglycogen is modified. Functionalization can be carried out on the surface of the nanoparticle, or on both the surface and the interior of the particle, but the structure of the glycogen or phytoglycogen molecule as a single branched homopolymer is maintained. In one embodiment, the functionalization is carried out on the surface of the nanoparticle.

When the polyfunctional glycogen or phytoglycogen additive will be used in food or personal care applications, chemical modifications should be non-irritating when in contact with human skin and/or safe when consumed as a food ingredient.

In some embodiments of the present invention, it is advantageous to change the chemical character of glycogen from its hydrophilic, slightly negatively charged native state to be positively and/or negatively charged, or to be partially or highly hydrophobic. Chemical processing of polysaccharides is well known in the art. See for example J. F Robyt, *Essentials of Carbohydrate Chemistry*, Springer, 1998; and M. Smith, and J. March, March's Advanced Organic Chemistry: Reactions, Mechanisms, and Structure Advanced Organic Chemistry, Wiley, 2007.

The nanoparticles can be either directly functionalized or indirectly, where one or more intermediate linkers or spacers can be used. The nanoparticles can be subjected to one or more than one functionalization steps including two or more, three or more, or four or more functionalization steps.

Various derivatives can be produced by chemical functionalization of hydroxyl groups of glycogen. Such functional groups include, but are not limited to, nucleophilic and electrophilic groups, and acidic and basic groups, e.g., carbonyl groups, amine groups, thiol groups, carboxylic groups, and hydrocarbyl groups such as alkyl, vinyl and allyl groups. Amino groups can be primary, secondary, tertiary, or quaternary amino groups.

In one embodiment, the polyfunctional glycogen or phytoglycogen additive is modified using various derivatives of succinic acid to increase its hydrophobicity. In one embodiment, glycogen is modified using octenyl succinic acid (OSA), resulting in glycogen with partially hydrophobic functionality, with the degree of substitution between 0.1 and 0.4.

Functionalized nanoparticles can be further conjugated with various desired molecules, which are of interest for a variety of applications, such as biomolecules, small molecules, therapeutic agents, micro- and nanoparticles, pharmaceutically active moieties, macromolecules, diagnostic labels, chelating agents, dispersants, charge modifying agents, viscosity modifying agents, surfactants, coagulation agents and flocculants, as well as various combinations of these chemical compounds.

Known methods for polysaccharide functionalization or derivatization can be used. For example, one approach is the introduction of carbonyl groups, by selective oxidation of glucose hydroxyl groups at positions of C-2, C-3, C-4 and/or C-6. There is a wide spectrum of oxidative agents which can be used such as periodate (e.g., potassium periodate), bromine, dimethyl sulfoxide/acetic anhydride (DMSO/$Ac_2O$) [e.g., U.S. Pat. No. 4,683,298], Dess-Martin periodinane, etc.

The nanoparticles described herein when functionalized with carbonyl groups are readily reactive with compounds bearing primary or secondary amine groups. This results in imine formation which can be further reduced to amine with a reductive agent e.g., sodium borohydrate. Thus, the reduction step provides an amino-product that is more stable than the imine intermediate, and also converts unreacted carbonyls in hydroxyl groups. Elimination of carbonyls significantly reduces the possibility of non-specific interactions of derivatized nanoparticles with non-targeted molecules, e.g. plasma proteins.

The reaction between carbonyl- and amino-compounds and the reduction step can be conducted simultaneously in one vessel (with a suitable reducing agent introduced to the same reaction mixture). This reaction is known as direct reductive amination. Here, any reducing agent, which selectively reduces imines in the presence of carbonyl groups, e.g., sodium cyanoborohydrate, can be used.

For the preparation of amino-functionalized nanoparticles from carbonyl-functionalized nanoparticles, any ammonium salt or primary or secondary amine-containing compound can be used, e.g., ammonium acetate, ammonium chloride, hydrazine, ethylenediamine, or hexanediamine. This reaction can be conducted in water or in an aqueous polar organic solvent e.g., ethyl alcohol, DMSO, or dimethylformamide.

Reductive amination of the nanoparticles described herein can be also achieved by using the following two step process. The first step is allylation, i.e., converting hydroxyls into allyl-groups by reaction with allyl halogen in the presence of a reducing agent, e.g., sodium borohydrate. In the second step, the allyl-groups are reacted with a bifunctional aminothiol compound, e.g., aminoethanethiol.

Amino-functionalized nanoparticles are amenable to further modification. For example, amino groups are reactive to carbonyl compounds (aldehydes and ketones), carboxylic acids and their derivatives, (e.g., acyl chlorides, esters), succinimidyl esters, isothiocyanates, sulfonyl chlorides, etc.

In certain embodiments, the nanoparticles described herein are functionalized using the process of cyanylation. This process results in the formation of cyanate esters and imidocarbonates on polysaccharide hydroxyls. These groups react readily with primary amines under very mild conditions, forming covalent linkages. Cyanylation agents such as cyanogen bromide, and, preferably, 1-cyano-4-diethyl-amino-pyridinium (CDAP), can be used for functionalization of the nanoparticles.

Functionalized nanoparticles can be directly attached to a chemical compound bearing a functional group that is capable of binding to carbonyl- or amino-groups. However, for some applications it may be important to attach chemical compounds via a spacer or linker including for example a polymer spacer or a linker. These can be homo- or hetero-bifunctional linkers bearing functional groups which include, but are not limited to, amino, carbonyl, sulfhydryl, succimidyl, maleimidyl, and isocyanate e.g., diamino-hexane, ethylene glycobis(sulfosuccimidylsuccinate) (sulfo-EGS), disulfosuccimidyl tartarate (sulfo-DST), dithiobis (sulfosuccimidylpropionate) (DTSSP), aminoethanethiol, and the like.

In certain embodiments, small molecule modifiers of the nanoparticles described herein can be those which can be useful as catalysts and include, but are not limited to, metal-organic complexes.

In certain embodiments, pharmaceutically useful moieties used as modifiers for the nanoparticles include, but are not limited to, hydrophobicity modifiers, pharmacokinetic modifiers, biologically active modifiers and detectable modifiers.

In certain embodiments, the nanoparticles can be modified with chemical compounds which have light absorbing, light emitting, fluorescent, luminescent, Raman scattering, fluorescence resonant energy transfer, and electroluminescence properties.

In certain embodiments, two or more different chemical compounds are used to produce multifunctional derivatives.

In one embodiment, the polyfunctional glycogen or phytoglycogen additive described herein is in the form of dry powder or granulate. The polyfunctional additive is readily dispersible in water and can be mixed directly with the aqueous phase by vigorous stirring. It requires neither pre-dispersion nor neutralization and can be hot or cold processed.

In one embodiment, the polyfunctional additive is provided in the form of a water solution having a concentration of up to 25% w/w. In one embodiment, the polyfunctional additive is provided in the form of a gel or semi-solid having a concentration of up to 35% w/w.

The present invention encompasses water-based and alcohol-based formulations that include the polyfunctional glycogen or phytoglycogen additive.

In one embodiment, the formulations include a natural gum.

In one embodiment, the composition is a food, a cosmetic, a personal care product, a nutraceutical, a pharmaceutical, a lotion, a gel, a paint, a coating, an ink, a lubricant, an excipient, a surface film, a stabilizer, or a drilling mud.

Emulsion formulations containing alcohols dissolved into the water phase are often used in spray-on cosmetic products, e.g. sunscreens, antiperspirants, aftershaves, hand sanitizers, etc. This allows fast drying of such formulations on the skin surface. However, fabrication of such alcohol-containing formulations presents a challenge, as it is difficult to incorporate lipophilic (oil soluble) compounds into aqueous alcohol-based emulsion formulations, and it is often not possible to obtain stable emulsions. It is believed that such emulsions are usually very unstable due to low surfactant adsorption at oil-alcohol interfaces.

In one embodiment, the formulation comprises an oil in alcohol dispersion. In one embodiment, the alcohol is not particularly restricted and suitable alcohols may be selected by those of skill in the art based on the use of the composition. In one embodiment, the alcohol is ethyl alcohol, propyl alcohol, isopropyl alcohol, ethylene glycol, propylene glycol, butylene glycol, dipropylene glycol, ethoxydiglycol, glycerol or a combination thereof.

The present inventors have demonstrated that hydrophobically-modified glycogen (e.g., OSA-modified glycogen) allows the incorporation of oily compounds such as emollients, sunscreen agents, perfumes (fragrances), vitamins A, D and E, essential oils, etc. into aqueous alcohol-containing formulations, which significantly reduces or even eliminates the need for emulsifiers and solubilizing additives. The present inventors found that the addition of OSA-modified glycogen with degrees of substitution ranging from 0.05 to 0.3 results in stable dispersions in aqueous alcohol solutions with alcohol content up to 85%. The alcohol used in these solutions was selected from the following: ethyl alcohol, propyl alcohol, isopropyl alcohol, ethylene glycol, propylene glycol, butylene glycol, dipropylene glycol, ethoxydiglycol, etc., and combinations of these alcohols. Furthermore, the low viscosity of aqueous alcohol formulations containing hydrophobically-modified glycogen makes it possible to use these formulations for spray-on applications for cosmetic, personal care and other products.

In one embodiment, the composition has improved solubility and stability compared to the same composition without the polyfunctional additive.

In one embodiment, the composition is a spray on personal care product. In one embodiment, the spray on personal care product is a spray on cosmetic, a spray on sunscreen, a hairspray, a spray on deodorant, a spray on antiperspirant, a spray on aftershave or a spray on hand sanitizer.

Rheology

Figure 2:
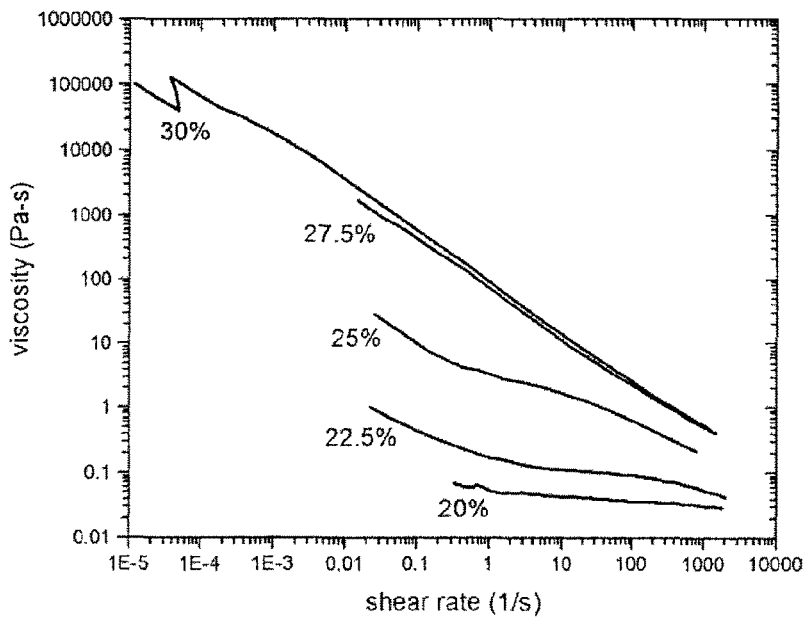
FIG. 2 shows the shear rate dependence on viscosity of a dispersion of monodisperse phytoglycogen nanoparticles in water.
Figure 3:
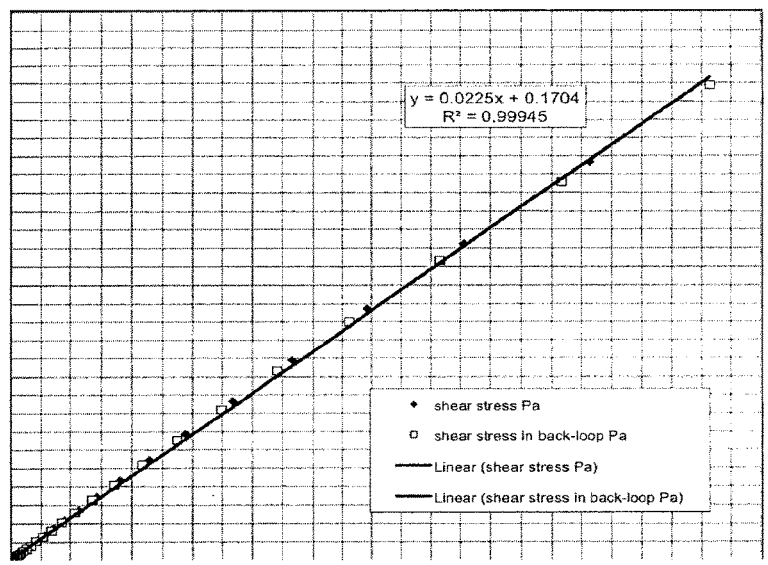
FIG. 3 shows the flow behavior of a dispersion of monodisperse phytoglycogen nanoparticles at 19% (w/w) is independent of shear rate.

In one embodiment, the polyfunctional additive is a monodisperse composition of phytoglycogen nanoparticles. In one embodiment, this monodisperse composition of phytoglycogen nanoparticles is prepared by methods disclosed in the international patent application entitled "Phytoglycogen Nanoparticles and Methods of Manufacture Thereof" being filed concurrently herewith by the same applicant, which methods include the method disclosed in Example 1 of this application. This additive is unique among the natural polymers in maintaining very low viscosities at up to 20-25% (w/w) concentration in water. Gums typically exhibit between 0.2 and 100 Pas viscosity values (at low shear rates) in 1% solutions. The polyfunctional additive reaches the 3 Pas viscosity value only at 25% concentration (w/w) (FIG. 1). For concentrations greater than 20% (w/w), suspensions display shear thinning behavior that increases with increasing concentration (FIG. 2). For concentrations less than 20% (w/w) of the polyfunctional additive, suspensions behave essentially as Newtonian fluids (viscosity and shear stress values are independent of the shear rate values) (FIG. 3). The viscosity of dispersions of the additive increases significantly above 25% (w/w), behavior that is unique to known phytoglycogen preparations. The viscosity profile of carbomers and polysaccharide gums (such as gum Arabic, carrageenan gum, xanthan gum) depends on pH, and electrolyte and salt concentration. This sensitivity to environmental conditions narrows the field of applications of these viscosity modifiers and complicates the formulation process. In contrast, the addition of salts does not significantly affect the viscosity profile of the polyfunctional additive described herein. Additionally, the viscosity profile of the polyfunctional additive is tolerant to pH changes in the range 3-9.

The viscosity values of dispersions of the polyfunctional additive show no significant dependence on the ionic strength.

Effect of Additive on Rheological Behaviour of Aqueous Dispersions

The present inventors have demonstrated that glycogen and phytoglycogen nanoparticles act as rheology modifiers when used as an additive in water-based and alcohol-based formulations and, in particular, solutions and dispersions of small molecules, polymers, biopolymers, colloidal particles or oils (e.g. emulsions). When used in suitable concentrations, the additive modulates viscosity and visco-elastic properties. Specific concentrations used will depend on the particular formulation used and are within the purview of a person of skill in the art. However, in one embodiment, the additive is used in an amount of up to 25% w/w based on the weight of the composition.

Time dependent rheological behaviour can be useful in food applications and in many other areas of industry, such as paint, coating, pharmaceutical, cosmetic applications where it can be highly desirable for a product to have a thick, high viscosity texture but to become liquid-like and easily pourable after shaking and then regaining its original properties shortly after it is allowed to rest.

When increasing the rate of shear stress applied to a material results in decreasing viscosity, the phenomenon is called shear thinning (the material which exhibits shear thinning behaviour is called pseudoplastic). Since it takes time to rebuild the inner structure of a pseudoplastic material when the mixing stops, by definition all shear thinning compositions are thixotropic. The time required for "re-thickening" is key in practical applications. The term of thixotropy is used when re-thickening takes a noticeable time by simple observation.

In one embodiment, the polyfunctional additive of the present invention modifies rheological properties in response to shear in the form of shear thinning. In one embodiment, the polyfunctional additive provides time dependent rheological behavior. In one embodiment, the polyfunctional additive increases re-thickening time when it is present in an already pseudoplastic system. In one embodiment, the polyfunctional additive imparts thixotropic behavior in other viscoelastic systems.

Natural gums are widely used by the cosmetic, food and other industries as thickeners, stabilizers, and gelling and emulsifier agents. Natural gums are polysaccharides and depending on their chemical nature and structure, the effect they exert can be modified by other components in a formulation. In an aqueous formulation, when more than one type of these water soluble natural gums are present, synergy is commonly observed. In a synergic interaction, viscosity values of 10-50 times higher than the added individual values can be obtained.

In one embodiment, the polyfunctional additive is used with water-based formulations comprising natural gums. Unlike other high molecular weight polysaccharides which can significantly enhance viscosity values, glycogen and phytoglycogen nanoparticles can produce unique changes in the properties of compositions comprising other gums and viscosity modifiers.

As demonstrated in the examples, the polyfunctional additive can be used to modify the time dependent rheological behaviour of natural gums in water-based dispersions. The modulus values of samples containing a polyfunctional additive of the present invention significantly dropped after pre-shear and the lost modulus values (G") became higher than the storage modulus values (G') (without the pre-shear G'>G"). This behaviour means a formulation becomes "liquid-like" when shaken and returns to its higher viscosity state on standing for a period of time. This behavior can be very beneficial in many food (like salad dressings, sauces, batters, gravies and so on) and also in cosmetic and pharmaceutical applications (lotions, gels).

Additive as a Stabilizer

The polyfunctional glycogen or phytoglycogen additive can be used as an ingredient to confer increased phase stability, increased heat stability, and increased stability in storage. Furthermore, the additive acts as a photostabilizer for photolabile compounds, which are commonly used in various cosmetics, medical and food formulations. The additive also provides improved emulsification and emulsion stabilization of oil in water emulsions, such as creams lotions etc. It can also be used in mixing procedures when other ingredients are introduced to the formulations as an additional step.

For personal care formulations, stability (physical, chemical and photochemical) is a critical factor. Temperature has a significant effect on stability. Introduction of different components into a formulation can have a significant effect on the viscosity and also on the stress and temperature tolerance of an emulsion.

Viscosity hysteresis is common when cycling between heating and cooling phases during temperature cycling tests. The less hysteresis observed, the better the emulsion tolerance to the heating stress. It is also important that viscosity returns to the original values after heating and cooling cycles, since if viscosity does not return to the same value, it indicates that some undesirable changes have occurred. Such "temperature cycling" tests are designed to reproduce real life conditions, where products can undergo significant temperature variations between manufacturing, shipping, storage, shelf-time, customer use, etc.

The present inventors have shown that the glycogen or phytoglycogen polyfunctional additive described herein improves emulsion stability on temperature cycling and delays or prevents the "melting" (crossing between G' and G") of oil in water emulsions in the temperature range of 0-50° C.

When different methods are used for introducing new components into a formulation, the nature of the procedure can significantly affect the rheological properties of the product but the polyfunctional additive described herein can provide protection against this phenomenon.

In the preparation of emulsion-based cosmetic, food and pharmaceutical formulations (typically oil-in-water emulsions), it is necessary to heat both water and oil phases above 50° C. to create a well-mixed emulsion (base emulsion). However, sometimes it is desirable to introduce additional thermo-labile (heat sensitive), water-soluble components, e.g., preservatives, bioactives, fragrances, etc. into the formulations at lower temperatures, e.g. temperatures below 35° C. This can be achieved by cooling the base emulsion and mixing-in a third, water-based phase containing the heat sensitive ingredients. However, the viscosity of the end product will strongly depend on the mechanical technique used to mix the third phase into the base emulsion.

The presence of a glycogen or phytoglycogen polyfunctional additive as described herein improves tolerance of the emulsions to mechanical stresses and enables faster, high-energy mixing techniques, e.g. homogenizers.

UV Protection

The glycogen or phytoglycogen polyfunctional additive described herein increases the SPF index of sun protection formulations whether based on physical (containing inorganic pigments) or chemical (containing UV-absorbing chemicals) sunscreen agents.

The damaging effects of over-exposure of human skin to sunlight are well known. Ultraviolet (UV) radiation (290-400 nm) is the most harmful part of the solar light spectrum. To protect human skin from harmful sunlight radiation, a wide variety of sunscreen preparations, based on physical and chemical agents, have been developed. To achieve adequate SPF, high concentrations of sunscreens need to be used in a formulation. However, regulatory agencies, e.g., FDA, limit sunscreen concentration to maxima of 3-15% based on component safety data. As a consequence, formulations have to contain a large number of different sunscreen actives.

Modified (octenylsuccinic acid) and un-modified glycogen and phytoglycogen additives have been incorporated by the present inventors into sunscreen formulations containing homosalate or titanium dioxide. Resulting sunscreen formulations demonstrate higher SPF values and improved photostability.

Photostabilization of Formulations

As shown in the examples, the present inventors have demonstrated that polyfunctional additives of glycogen and phytoglycogen nanoparticles according to the present invention act as a photostabilizer.

The photostabilizing effect of the polyfunctional additive of the present invention is of particular utility in the case of organic sunscreen formulations. Numerous recent studies have demonstrated that many sunscreen actives suffer from inadequate photostability and rapidly lose their photoprotective ability upon ultraviolet irradiation. This results in marketed products that may not meet their labeled SPF index. Furthermore, photoinactivation of sunscreens may produce free radical intermediates and compounds that act as sensitizers and photoallergens.

The present inventors have shown that the photostability of sunscreen organic actives can be enhanced by the introduction of phytoglycogen into sunscreen formulations.

These results show that the SPF value of the irradiated formulations was considerably higher using phytoglycogen or OSA-modified phytoglycogen. The choice of using phytoglycogen or OSA-modified phytoglycogen will depend on the particular organic sunscreen compound. To improve photostability and dispersibility, sunscreen actives can also be covalently conjugated to phytoglycogen.

Without wishing to be bound by a theory, it is believed that the higher SPF value reflects both an improvement of the photostability of the sunscreen filters and an increase in the overall opacity of the film for the dehydrated formulation.

Humectant

The glycogen or phytoglycogen polyfunctional additive of the present invention shows enhanced water retention properties when compared to other well-known moisturizing agents.

Without wishing to be bound by a theory, this unique water retention ability is likely due to the physical structure of the glycogen or phytoglycogen nanoparticles. Each particle is a semi-rigid structure laced with pores. Since the glycogen or phytoglycogen nanoparticles are built from sugars, and sugars are highly hydrophilic, it seems reasonable to assume that water enters the pores of the particles and is strongly held there. Thus it is likely the combination of the unique nano-physical structure and the inherent properties of sugars that provides the unique capability to hold water.

The present inventors calculated from viscosity measurements that when the glycogen or phytoglycogen nanoparticles are fully hydrated ~62% of their volume is filled with water and 1.64 g water/g glycogen is part of the hydrated glycogen structure. When the glycogen or phytoglycogen nanoparticle additive is allowed to come to equilibrium in a high moisture (98% RH) environment, it will absorb ~50% of its own weight in water.

EXAMPLE 1

Extraction of Phytoglycogen from Sweet Corn Kernels 1 kg of frozen sweet corn kernels (75% moisture content) was mixed with 2 L of deionized water at 20° C. and was pulverized in a blender at 3000 rpm for 3 min. Mush was centrifuged at 12,000×g for 15 min at 4° C. The combined supernatant fraction was subjected to CFF using a membrane filter with 0.1 µm pore size. The filtrate was further purified by a batch diafiltration using membrane with MWCO of 500 kDa and at RT and diavolume of 6. (Diavolume is the ratio of total mQ water volume introduced to the operation during diafiltration to retentate volume.)

The retentate fraction was mixed with 2.5 volumes of 95% ethanol and centrifuged at 8,000× g for 10 min at 4° C. The retentate was mixed with 2.5 volumes of 95% ethanol and centrifuged at 8,000×g for 10 min at 4° C. The pellet containing phytoglycogen was dried in an oven at 50° C. for 24 h and then milled to 45 mesh. The weight of the dried phytoglycogen was 97 g.

According to DLS measurements, the phytoglycogen nanoparticles produced had particle size diameter of 83.0 nm and the polydispersity index of 0.081.

EXAMPLE 2

Modification of Phytoglycogen by its Reaction with Octenyl-succinic Anhydride in Water 100.0 g of phytoglycogen produced according to Example 1 was dispersed in 750 mL of deionized water in a 2 L glass reaction vessel. The dispersion was constantly stirred and kept at 35° C. 50 mL of octenyl succinic anhydride (OSA, Sigma-Aldrich) was heated to 40° C. and was pumped into the reaction vessel. The pH was kept constant at 8.5 by adding a 4% NaOH solution to the reaction mix using an automated control system. After 100 min, the OSA pumping was stopped, and the reaction was allowed to proceed for an additional 2.5 h. Then the pH of the mixture was adjusted to 7.0 with 1 M HCl and was mixed with 3 volumes of 95% ethanol and centrifuged at 8,500×g for 15 min at 4° C. The pellet was re-suspended in water, the pH was adjusted to 7.0, and the solution was precipitated and centrifuged using the same conditions twice. Finally, the pellet containing OSA-modified phytoglycogen was dried in an oven at 50° C. for 24 h and then milled to 45 mesh. The degree of substitution determined by NMR spectroscopy was 0.27.

EXAMPLE 3

Glycogen/Phytoglycogen as a Non-thickening Rheology-modifying Additive that Imparts Thixotropy (Oscillatory Sweep Test)

Aqueous dispersions of 0.7% (w/w) konjac gum and 0.7% (w/w) konjac gum plus 0.7% concentration (w/w) phytoglycogen prepared according to Example 1 were used for the rheology tests.

Konjac gum is used by the food industry as a gelling agent, thickener, stabilizer, emulsifier and film former. Chemically it is a high molecular weight polysaccharide consisting primarily of mannose and glucose sugars (Glucomannan). The gum is also used in cosmetic formulations either alone or in combination with other natural gums.

The measurements were performed on a RA 2000 Rheometer (TA Instruments-Waters LLC), using a cone-plate geometry (4 cm dia plate, 1.58° steel cone; truncation gap=50.8 μm). The tests were run at 20° C. After loading the samples, there was a 4 min equilibration time, and then the stress sweep was performed at 1 Hz from 1 to 10,000 μNm (torque range). Data were collected in log mode (10 points per decade). In runs in which pre-shear was applied before the running of the stress sweeps, the compositions were subjected to a 10 Hz pre-shear for 6 min.

It was found that the viscosity of the konjac gum dispersions did not show sensitivity to pre-shear. However, pre-shearing caused drastic changes in its stress tolerance when the phytoglycogen was present: the modulus values of the samples containing phytoglycogen decreased significantly after pre-shear was applied, and the loss modulus values (G") became larger than the storage modulus values (G'), indicating a more "liquid-like" behaviour. Without the pre-shear, G' was greater than G".

A formulation with this behaviour becomes "liquid-like" when mixed or shaken, and returns to its higher viscosity state after a period of time. This behavior can be very beneficial in many food (e.g., salad dressings, sauces, batters, etc.), cosmetic and pharmaceutical applications (lotions, gels), in paints, coatings and inks, and in drilling muds in the petrochemical industry. This experiment indicates that the polyfunctional additive of the present invention can be used as a non-thickening rheology modifier, which imparts desirable rheological properties to a variety of industrial product formulations.

EXAMPLE 4

Glycogen/Phytoglycogen as a Non-thickening Rheology-modifying Additive that Imparts Thixotropy (Peak-hold Test)

The test compositions, used in these experiments were 0.5% (w/w) konjac gum, either without glycogen/phytoglycogen or with an additional 0.5% (w/w) phytoglycogen prepared according to Example 1.

The measurements were performed using a RA 2000 Rheometer (TA Instruments-Waters LLC), using a cone-plate geometry (4 dia cm, 1.58° steel cone; truncation gap=50.8 μm). The tests were performed at 20° C. After loading the samples, there was a 4 min equilibration time that was followed by a peak hold flow test using a 10 Hz shear rate for 1 h (sampling delay time of 10 s). After the peak hold test, a time sweep was conducted for 20 min at 1 Hz, using a 4 Pa oscillatory stress as a control variable (sampling delay time of 10 s).

Figure 4:
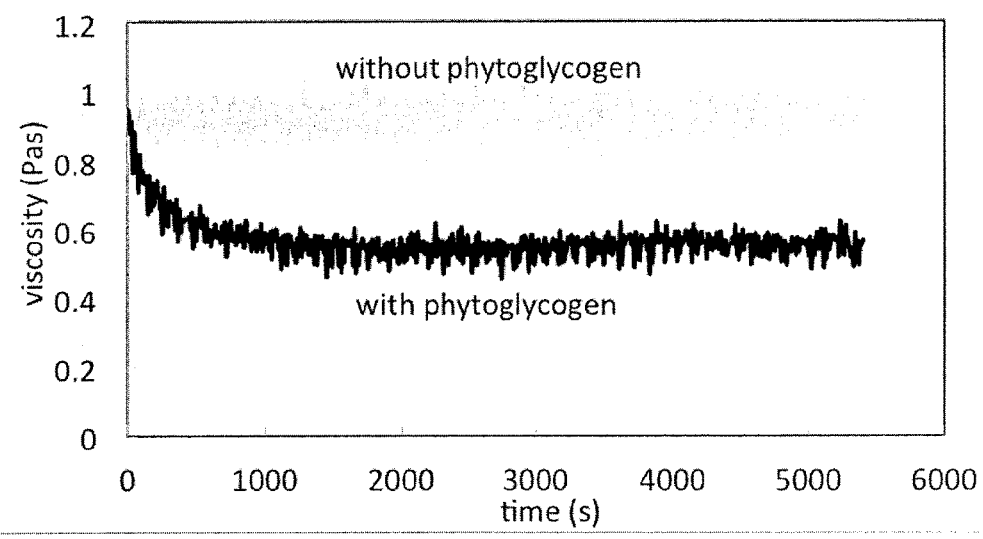
FIG. 4 shows peak hold flow tests of a 0.5% (w/w) konjac gum solution with and without 0.5% monodisperse phytoglycogen.

Formulations without phytoglycogen did not demonstrate thixotropic behaviour (see FIG. 4).

When phytoglycogen was present, a time dependent decrease in viscosity, corresponding to thixotropic behaviour, was observed (see FIG. 4), with the viscosity decreasing rapidly during the first 2-3 min of applied shear and reaching a steady state value after ~12 min. When shearing was stopped, the viscosity of the "undisturbed state" re-established in a short period of time (~2 min).

These data clearly indicate that the addition of a polyfunctional additive of the present invention imparts desirable thixotropic properties to formulations containing thickeners, e.g. gums.

EXAMPLE 5

Glycogen/Phytoglycogen as a Non-thickening Rheology Modifying Additive that Imparts Thixotropy (Step Flow Loops)

The compositions used in these tests contained 0.5% (w/w) konjac gum either without glycogen/phytoglycogen or with an additional 0.5% phytoglycogen prepared according to Example 1. Stepped flow loops were conducted with increasing shear rates (up flow) in the first part of the cycle, followed by decreasing shear rates (down flow) in the second part of the cycle.

The measurements were performed on a RA 2000 Rheometer (TA Instruments-Waters LLC), using a plate-cone geometry (4 dia cm, 1.58° steel cone; truncation gap=50.8 μm). The tests were performed at 20° C. After loading the samples there was a 4 min equilibration time that was followed by the stepped flow loop. In the first part of the cycle, the torque range was increased from 1 to 600 μNm. In the second part of the cycle, the torque range was decreased from 600 to 1 μNm (10 points per decade–log mode; constant time of 10 s; average over last 5 s).

Figures 5A, 5B:
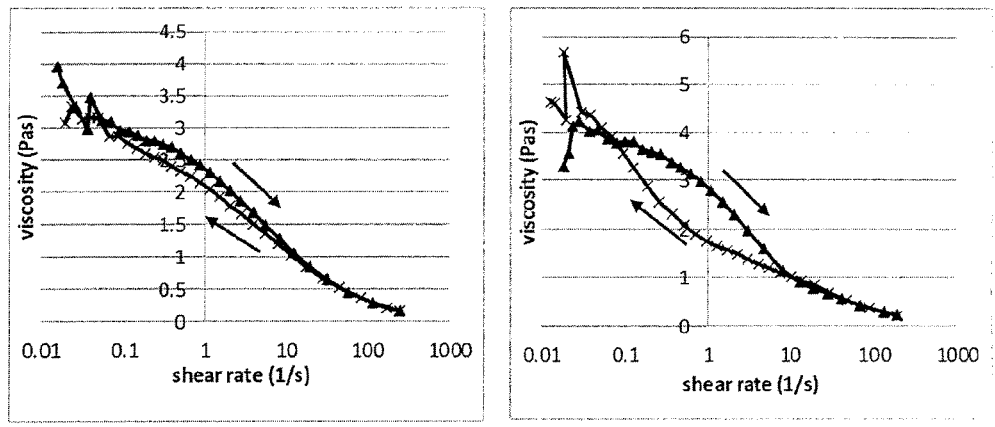
FIG. 5A shows viscosity values in stepped flow loops of compositions containing 0.5% konjac gum without a polyfunctional additive of the present invention.
FIG. 5B shows viscosity values in stepped flow loops of the compositions containing 0.5% konjac gum with 0.5% phytoglycogen.

Results of the measurements are presented in FIGS. 5A and 5B. The introduction of phytoglycogen to konjac gum in the aqueous solution resulted in a significant hysteresis loop between the up and down flow curves (FIG. 5B), compared to the results obtained for glycogen-free solutions (FIG. 5A). The difference between the viscosity values measured for up flow and down flow with a polyfunctional additive of the present invention present in the formulations indicates that, after shear thinning is observed with increasing flow rate, a polyfunctional additive of the present invention increases the rebuilding time and renders the system thixotropic.

EXAMPLE 6

Glycogen/Phytoglycogen as a Rheology Stabilization Additive for Emulsion-based Formulations that Provides Temperature Stress Tolerance The effect of glycogen/phytoglycogen on the rheological properties of cosmetic formulations was investigated using a commercially available "Balanced cream base" from MakingCosmetics Inc., Renton Wash., USA.

Ingredients (from the manufacturer): water, isopropyl palmitate, jojoba oil, caprylic capric triglyceride, squalane, 1,3 propanediol, ceteareth-20, dimethicone, glyceryl stearate, raspberry seed oil, cetearyl alcohol, peg-100 stearate, sodium lauryl lactylate, octyl dodecanol, beeswax, ethylhexylglycerin, caprylyl glycol, tocopheryl acetate, hydroxyethyl cellulose, hexylene glycol, disodium EDTA, tocopherol, ascorbyl palmitate, ascorbic acid, citric acid, methylisothiazolinone.

The manufacturer intends that this formulation will be customized by adding up to 15-20% (volume percentage) of additional liquid ingredients, such as active ingredients and/or fragrances, without excessive thinning of the cream.

Sample Preparation:

Formulation 1: The cream base was combined with Milli-Q water (resistivity of 18.2 MΩ-cm) in the ratio of 9:1 (w/w).

Formulation 2: The cream base was combined with a solution of 22% (w/w) phytoglycogen (prepared according to Example 1) in Milli-Q water in the ratio of 9:1 (w/w; final phytoglycogen concentration in the cream is 2.2%).

Formulation 3: The cream base was combined with a solution of 22% OSA-modified phytoglycogen (prepared according to Example 2) in Milli-Q water in the ratio of 9:1 (w/w; final OSA-modified phytoglycogen concentration in the cream is 2.2%).

"Temperature cycling" measurements were performed using a RA 2000 Rheometer (TA Instruments-Waters LLC), using a cone-plate geometry (4 dia cm, 1,58° steel cone; truncation gap=50.8 μm). The samples were loaded onto the cold geometry and, after a 3 min equilibration time once the temperature reached 0° C., a 5 min pre-shear was performed (10 Hz). The temperature was first increased from 0° C. to 50° C., with 5° C. increments (heating cycle), and a 3 min equilibration time after each increment. The temperature was then decreased from 50° C. to 0° C. (cooling cycle) in the same manner (5° C. increments, with a 3 min equilibration time). The tests were run at 1 Hz. Two values of the torque were used: 200 μNm ("high-torque") and 20 μNm ("low-torque"). Fresh samples were used for each "high-torque" and "low-torque" measurement.

It is common to see viscosity hysteresis between the heating and cooling phases during temperature cycling tests. The lower the hysteresis, the better the tolerance of the emulsion to the heating stress. It is also important that the viscosity recovers its original value after the heating and cooling cycles. If the viscosity value does not recover, this is an indication that an undesirable change has occurred. Such a "temperature cycling" test is designed to reproduce real life conditions, in which an emulsion-based product undergoes significant temperature variations during transportation between, for example, the manufacturing site, the warehouse and the retail store.

Figure 6:
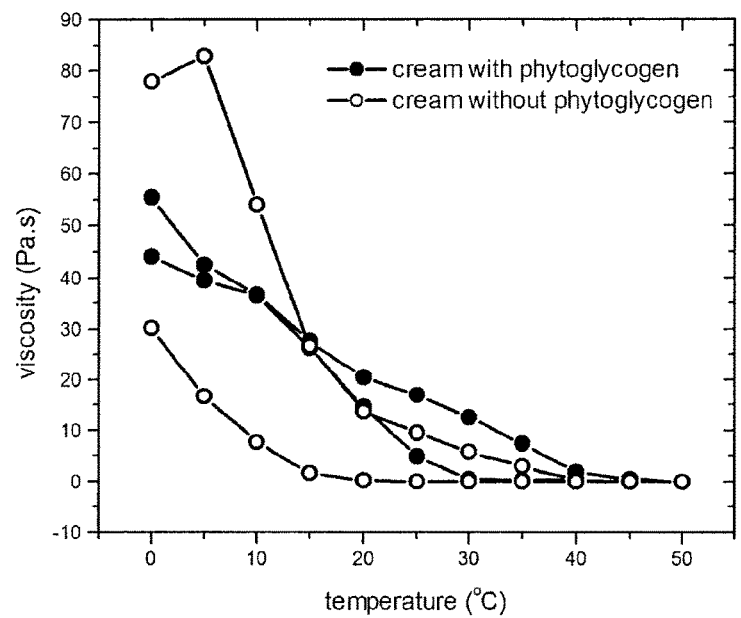
FIG. 6 compares viscosity values in a temperature sweep cycle between 0 and 50° C., with increasing temperature in the first part of the cycle and decreasing temperature in the second part of the cycle for cream base without a polyfunctional additive of the present invention (squares) and with a polyfunctional additive of the present invention (circles).
Figure 7:
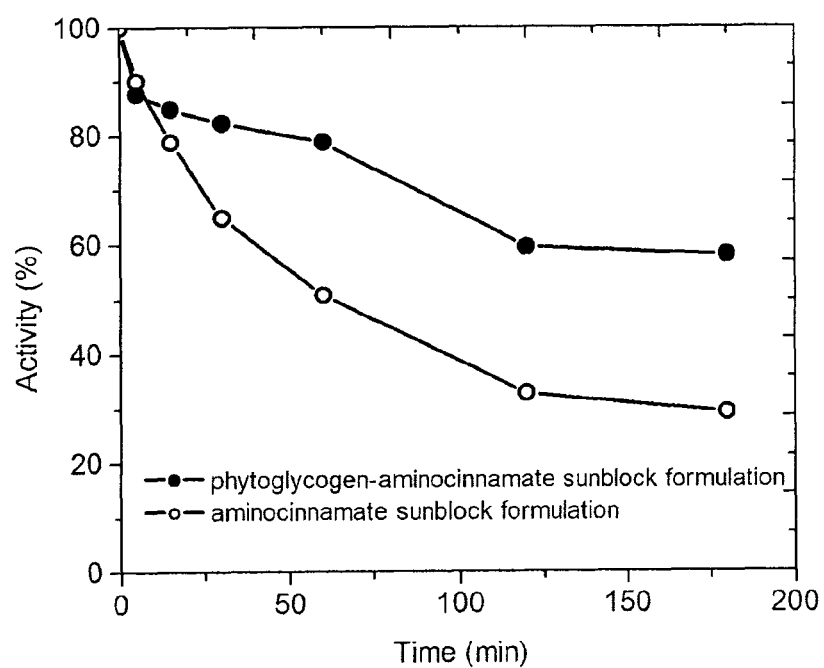
FIG. 7 shows photostability of aminocinnamate (diamonds) and a phytoglycogen-ethyl-4-aminocinnamate conjugate (squares).
Figure 8:
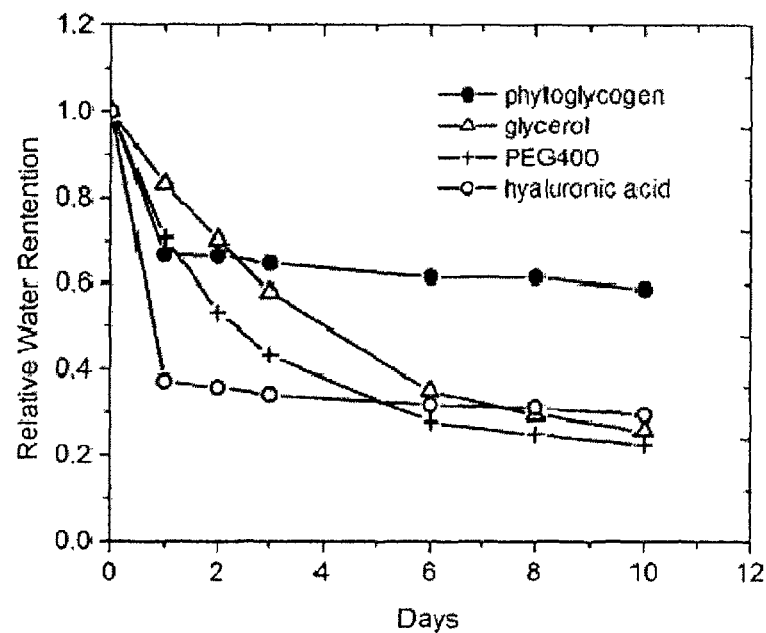
FIG. 8 shows relative water retention of a dried monodisperse phytoglycogen nanoparticle composition, glycerol, PEG 400 and hyaluronic acid.
Figure 9:
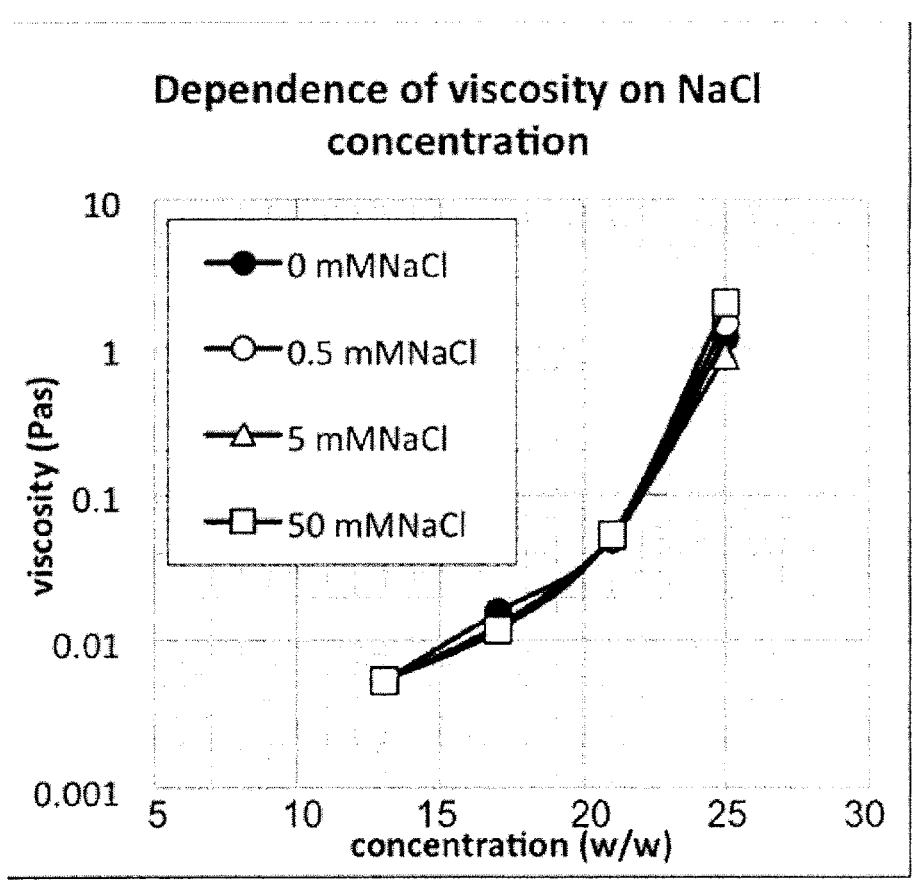
FIG. 9 shows the viscosity values of dispersions of monodisperse phytoglycogen nanoparticles show no significant dependence on the ionic strength.
Figure 10:
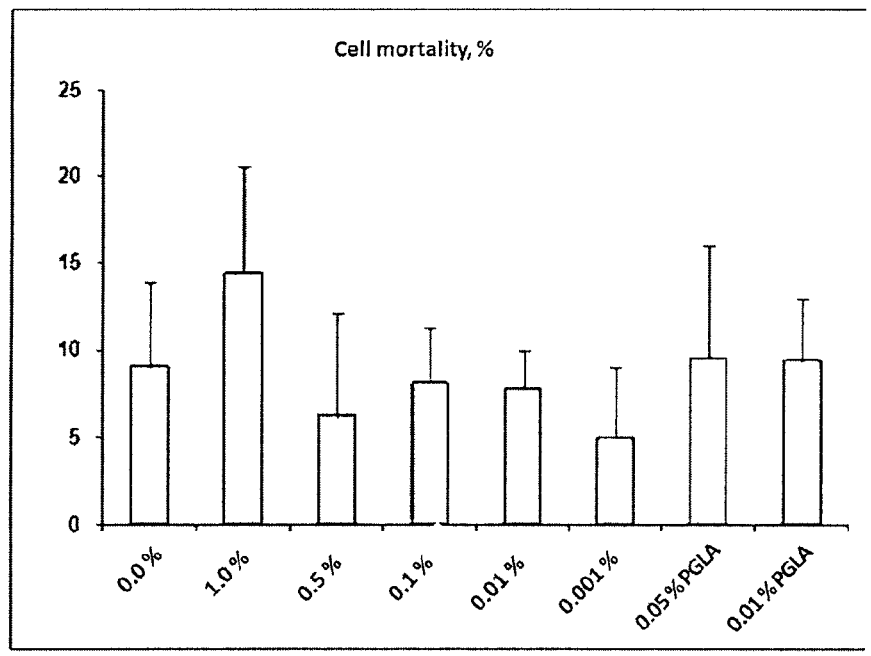
FIG. 10 shows the cytotoxicity as measured by dead cells of monodisperse glycogen nanoparticles (nps) on Hep2 (cancer liver cells) as compared to poly(lactic-co-glycolic acid) (PLGA).
Figure 11:
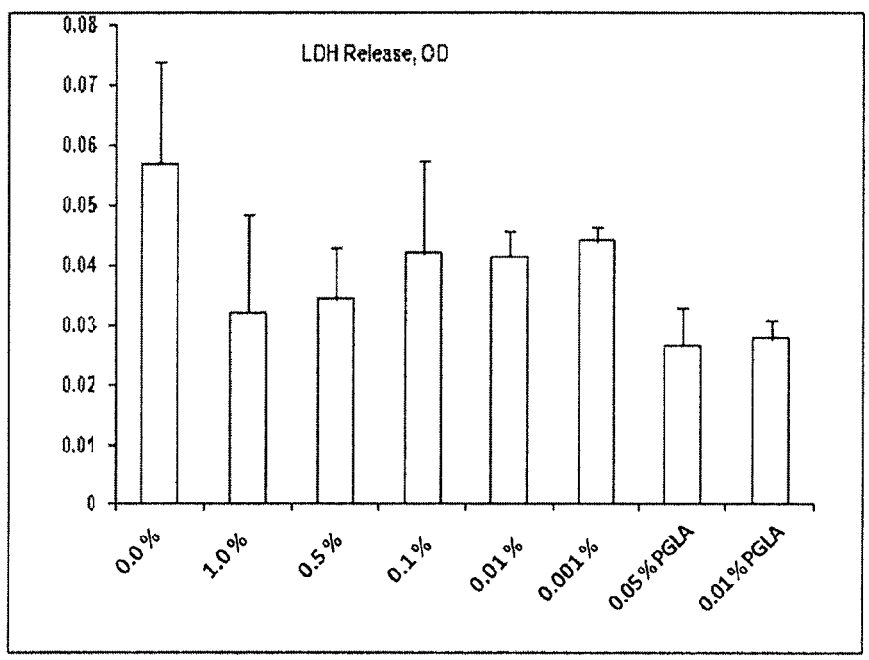
FIG. 11 shows the cytotoxicity as measured by release of LDH (lactate dehydrogenase) of monodisperse glycogen nanoparticles (nps) on Hep2 (cancer liver cells) as compared to poly(lactic-co-glycolic acid) (PLGA).

As can be seen from the data presented in FIG. 6 for the "high-torque" experiment, the hysteresis loop area is markedly smaller with phytoglycogen present in the formulation. Moreover, the viscosity recovered its initial value at the end of the heating and cooling cycle for Formulation 2 (containing phytoglycogen). In contrast, the viscosity of Formulation 1 without phytoglycogen was significantly lower than the viscosity at the start of the temperature cycle, which is possibly due to partial demulsification of Formulation 1. This indicated that phytoglycogen improved the emulsion stability with temperature cycling.

Formulations 1, 2 and 3 were subjected to the "low-torque" test, and measurements of the storage (G') and loss (G") modulus values were measured. For Formulation 1, which does not contain phytoglycogen, a large hysteresis between the heating and cooling cycles was observed for both G' and G" modulus values. Modulus values at the end of the temperature cycling were significantly lower than at the start, indicating possible undesirable demulsification. A significant hysteresis was also observed for Formulation 3 (containing OSA-modified phytoglycogen), since modulus values at the end the temperature cycling were larger than at the start but its presence prevented the cross over between the moduli values. Tests of Formulation 2 (containing phytoglycogen) showed the lowest hysteresis, with modulus values recovering their initial values after the experiment, and the loss modulus curve did not cross the storage modulus curve.

This result indicates that a polyfunctional additive of the present invention improves the stability of emulsion-based formulations during temperature cycling.

EXAMPLE 7

Glycogen/Phytoglycogen as a Rheology Stabilization Additive for Emulsion-based Formulations that Provides Tolerance to Mechanical Stress (Stress and Strain Tolerance)

The samples were prepared as in example 6.

The measurements were performed using a RA 2000 Rheometer (TA Instruments-Waters LLC), using a cone-plate geometry (4 dia cm, 1.58° steel cone; truncation gap=50.8 μm). The tests were performed at 20° C. After loading the samples, equilibration was allowed to occur for 5 min, and then the stress sweep was performed at 1 Hz using a torque range of 1 to 10,000 μNm. Data were collected in log mode (10 points per decade).

The presence of phytoglycogen or OSA-modified phytoglycogen increased the stability of the cream, as the linear viscoelastic region of these formulations extended to larger oscillatory stress or strain values when phytoglycogen or OSA-modified phytoglycogen was present.

This result indicates that a polyfunctional additive of the present invention both unmodified and OSA-modified provide greater stability with respect to changes in strain and stress.

EXAMPLE 8

Glycogen/Phytoglycogen as a Rheology Stabilization Additive for Emulsion-based Formulations that Provides Tolerance to Mechanical Stress To investigate the influence of different methods for the introduction of new components, the formulations were prepared according to Example 6, but using two different mixing methods. The formulations were mixed either by using low shear mechanical stirring or a high-energy homogenizer (IKA T18 Basic Ultra Turrax). Use of a homogenizer is more desirable in the preparation of various emulsion-based products because it allows fast mixing and a corresponding reduction of the preparation time.

Oscillatory stress tests were used to assess the possible effect of phytoglycogen on the formulation when mixing methods with substantially different energy inputs and times necessary to complete the process were used for further customizing the base cream.

The measurements were performed using a RA 2000 Rheometer (TA Instruments-Waters LLC), using a cone-plate geometry (4 dia cm, 1.58° steel cone; truncation gap=50.8 µm). The tests were performed at 20° C. After loading the samples, equilibration was allowed to occur for 5 min, and then the stress sweep was performed at 1 Hz using a torque range of 1 to 10,000 µNm. Data were collected in log mode (10 points per decade).

Preparation of Formulation 1 (without glycogen/phytoglycogen) using the high-energy homogenizer resulted in an undesirable 10-fold reduction in the viscosity of the formulation compared with that of Formulation 1 prepared using low shear mechanical stirring (3 Pa*s versus 30 Pa*s). By incorporating phytoglycogen (prepared according to Example 1) into the formulation (Formulation 2), the viscosity value obtained using the homogenizer was much closer to that obtained using low shear mechanical stirring (20 Pa*s versus 27 Pa*s). This result demonstrated that incorporation of phytoglycogen dramatically improved the stability of the emulsion to mechanical stresses. Incorporation of OSA-modified phytoglycogen (prepared according to Example 2) (Formulation 3) also resulted in reduced drop in the viscosity introduced by high-energy mixing using the homogenizer (3.4 Pa*s for the homogenizer versus 11 Pa*s for low shear mechanical stirring), but the effect was not as dramatic as for unmodified phytoglycogen (Formulation 2).

In control experiments (no additive), the use of a high-shear homogenizer resulted in undesirable decreases in viscosity of the final emulsion. In contrast, simple mechanical stirring did not produce such drastic decreases in viscosity, but required an undesirably long time to mix the phases. However, incorporating the polyfunctional additive described herein into the formulation allowed the use of high energy mixing techniques.

This experiment demonstrates that the presence of a polyfunctional additive of the present invention improves the tolerance of emulsions to mechanical stresses and allows faster, high-energy mixing techniques, e.g. homogenizers, to be used.

EXAMPLE 9

Glycogen/Phytoglycogen Improves Sun-protection Properties of Organic Sunscreen Formulations Phytoglycogen and phytoglycogen modified with octenylsuccinic acid (OSA-modified glycogen) were incorporated into sunscreen formulations containing homosalate (a UV-absorbing compound) as described below.

TABLE I

Sunscreen Formulation.

| | | % wt|wt | | |
|---|---|---|---|---|
| Phase | Ingredient | I | II | III |
| Oil | Lanolin | 4.25 | 4.25 | 4.25 |
| | Petrolatum | 2.6 | 2.6 | 2.6 |
| | Stearic acid | 3.5 | 3.5 | 3.5 |
| | Stearyl palmitate | 1.7 | 1.7 | 1.7 |
| | Behenyl alcohol | 0.9 | 0.9 | 0.9 |
| | Propyl Parahydroxybenzoate | 0.05 | 0.05 | 0.05 |
| | Homosalate | 7.0 | 7.0 | 7.0 |
| Water | Deionized water | 73.65 | 67.65 | 67.65 |
| | Propylene glycol | 5.0 | 5.0 | 5.0 |
| | Phytoglycogen | | 6.0 | |
| | OSA-modified glycogen | | | 6.0 |
| | Xanthan gum | 0.2 | 0.2 | 0.2 |
| | Triethanolamine | 1.0 | 1.0 | 1.0 |
| | EDTA | 0.05 | 0.05 | 0.05 |
| | Methyl Parahydroxybenzoate | 0.1 | 0.1 | 0.1 |

Phytoglycogen was extracted from sweet corn as described in Example 1. OSA-modified phytoglycogen was prepared as described in Example 2 and the resulting degree of substitution was 0.27.

Both phases (the water and oil phases) were heated to 83° C. with constant stirring until completely melted/solubilised. The water phase was stirred with the high-energy homogenizer (IKA T18 Basic Ultra Turrax) at 24 Krpm for 2 min before mixing with the oil phase. The oil phase was then added into the water phase while stirring with the homogenizer at 24 Krpm for 2 min, cooled to 40° C. while slowly stirring, then stirred again with the homogenizer at 24 Krpm for 1 min.

The resulting sunscreen formulations were tested for the SPF value and photostability using an Optometrics SPF-290S spectrophotometer and an Ocean Optics UV-VIS spectrometer. The results of the tests are shown in Table II. The SPF boost values refer to the percentage increase in the SPF value relative to the formulation that did not contain phytoglycogen or OSA-modified phytoglycogen.

TABLE II

| | Sunscreen actives | SPF | Crit wavelength, nm | SPF boost, % |
|---|---|---|---|---|
| I | Homosalate | 2.09 | 328 | 0 |
| II | Homosalate + phytoglycogen | 2.22 | 329 | 6.2 |
| III | Homosalate + OSA-modified phytoglycogen | 2.40 | 328 | 14.8 |

EXAMPLE 10

Glycogen/Phytoglycogen Improves the Sun-protection Properties of Inorganic Sunscreen Formulations Phytoglycogen and OSA-modified phytoglycogen were incorporated into sunscreen formulations containing titanium dioxide using a similar procedure to that described in Example 9. The contents of the formulations are described in Table III.

TABLE III

| Phase | Ingredient | % wt/wt I | II | III |
|---|---|---|---|---|
| Oil | Lanolin | 4.25 | 4.25 | 4.25 |
| | Petrolatum | 2.6 | 2.6 | 2.6 |
| | Stearic acid | 3.5 | 3.5 | 3.5 |
| | Stearyl palmitate | 1.7 | 1.7 | 1.7 |
| | Behenyl alcohol | 0.9 | 0.9 | 0.9 |
| | Propyl Parahydroxybenzoate | 0.05 | 0.05 | 0.05 |
| | Mineral oil | 7.0 | 7.0 | 7.0 |
| Water | Deionized water | 67.65 | 61.65 | 61.65 |
| | Propylene glycol | 5.0 | 5.0 | 5.0 |
| | Titanium dioxide | 6.0 | 6.0 | 6.0 |
| | Glycogen | | 6.0 | |
| | OSA-modified phytoglycogen | | | 6.0 |
| | Xanthan gum | 0.2 | 0.2 | 0.2 |
| | Triethanolamine | 1.0 | 1.0 | 1.0 |
| | EDTA | 0.05 | 0.05 | 0.05 |
| | Methyl Parahydroxybenzoate | 0.1 | 0.1 | 0.1 |

The resulting sunscreen formulations were tested for SPF and photostability using an Optometrics SPF-290S spectrophotometer and an Ocean Optics UV-VIS spectrometer. The results of the tests are shown in Table IV. The SPF boost values refer to the percentage increase in the SPF value relative to the formulation that did not contain phytoglycogen or OSA-modified phytoglycogen.

TABLE IV

| | Sunscreen actives | SPF | Crit wavelength, nm | SPF boost, % |
|---|---|---|---|---|
| I | $TiO_2$ | 2.37 | 388 | 0 |
| II | $TiO_2$ + phytoglycogen | 2.64 | 388 | 11.4 |
| III | $TiO_2$ + OSA-modified phytoglycogen | 2.78 | 388 | 17.3 |

EXAMPLE 11

Glycogen/Phytoglycogen Improves the Photostability of Organic Sunscreens

Phytoglycogen and OSA-modified phytoglycogen were incorporated into formulations containing chemical sunscreen actives as described in Example 9.

The formulations were deposited as thin films (surface coverage of 2-4 mg/cm$^2$) onto a quartz plate and dried in air for 30 min. After drying, the samples were irradiated with UV light (two UV lamps, 15 W, 254 nm, UVP Inc., part #34-000-801) for 4 h and then tested for their photostability by recording optical absorption spectra.

The photodegradation was calculated from the decrease in the maximum absorption of the respective products. Also, the change in the SPF value with time of irradiation was measured for the formulations as described in Examples 9 and 10. The results are shown in Tables V, VI, VII and VIII.

TABLE V

Homosalate photostability in formulations, without or with glycogen/phytoglycogen

| Sunscreen actives | Abs @ 308 nm | Abs @ 308 nm after 4 h of exposure | Change in Abs, % |
|---|---|---|---|
| Homosalate 7% | 1.0 | 0.86 | −24 |
| Homosalate 7% + phytoglycogen, 6% | 1.0 | 1.0 | 0 |
| Homosalate 7% OSA-modified phytoglycogen, 6% | 1.0 | 0.82 | −18 |

TABLE VI

Octyl methoxycinnamate photostability in formulations, without or with glycogen/phytoglycogen

| Sunscreen actives | Abs @ 316 nm | Abs @ after 4 h of exposure | Change in Abs, % |
|---|---|---|---|
| OM cinnamate 7% | 1.0 | 0.26 | −74.5 |
| OM cinnamate 7% + phytoglycogen, 6% | 1.0 | 1.30 | +30.0 |
| OM cinnamate 7% + OSA-modified phytoglycogen, 6% | 1.0 | 0.92 | −8.0 |

TABLE VII

Avobenzone photostability in formulations, without or with glycogen/phytoglycogen.

| Sunscreen actives | Abs @ 308 nm | Abs @ 308 nm after 4 h of exposure | Change in Abs, % |
|---|---|---|---|
| Avobenzone 7% | 1.0 | 0.46 | −54.0 |
| Avobenzone 7% + phytoglycogen, 6% | 1.0 | 1.08 | +8.0 |
| Avobenzone 7% OSA-modified phytoglycogen, 6% | 1.0 | 0.53 | −47.0 |

TABLE VIII

SPF boost in irradiated sunscreen compositions containing phytoglycogen and OSA-modified phytoglycogen.

| Sunscreen actives | SPF | SPF after 4 h of exposure | SPF boost, % |
|---|---|---|---|
| Homosalate 7% | 2.00 | 2.25 | 12.5 |
| Homosalate 7% + phytoglycogen, 6% | 2.45 | 4.2 | 71.2 |
| Homosalate 7% OSA-modified phytoglycogen, 6% | 3.0 | 4.5 | 50.0 |

These results show that the SPF value of the irradiated formulations was considerably higher using phytoglycogen or OSA-modified phytoglycogen. The choice of using an unmodified or OSA-modified polyfunctional additive will depend on the particular organic sunscreen compound.

EXAMPLE 12

Photostabilization of Vitamin a by OSA-modified Phytoglycogen

Vitamin A and OSA-modified phytoglycogen (prepared according to Example 2) were incorporated into alcohol-based emulsions. 24 mL of water or a 20% solution of OSA-modified phytoglycogen in water was added to 74 mL of 95% ethanol under constant stirring. Then 2 g of vitamin A (retinyl acetate) was added and the mixture was stirred with a high-energy homogenizer (IKA T18 Basic Ultra Turrax) at 24 Krpm for 4 min at room temperature. This produced a stable emulsion with low viscosity, which is suitable for spray application.

Measurements were conducted as described in Example 11. Photodegradation was calculated from the decrease in the maximum absorption at 371 nm for vitamin A and at 335 nm for vitamin A-OSA-modified phytoglycogen.

The results are shown in Table IX and they demonstrate that OSA-modified phytoglycogen dramatically improved the photostability of vitamin A. After 3 h of UV light irradiation, there was no measurable change in vitamin A concentration in the emulsion containing OSA-modified phytoglycogen, in contrast to a 56% decrease in vitamin A concentration in the emulsion that did not contain OSA-modified phytoglycogen.

TABLE IX

Vitamin A photostability in formulations, without or with OSA-modified phytoglycogen.

| Actives | Abs | Abs after 3 h of exposure | Change in Abs, % |
|---|---|---|---|
| Vitamin A, 2% | 1.0 | 0.44 | −56.0 |
| Vitamin A, 2% + OSA-modified phytoglycogen, 6% | 1.0 | 1.0 | 0 |

EXAMPLE 13

Method of Glycogen/Phytoglycogen Derivatization with Aminocinnamate 1 g succinoylated-phytoglycogen (DS=0.128) was dissolved in 12 ml of milliQ water and the pH was adjusted to 5. 150 mg ethyl 4-aminocinnamate was dissolved in 3 ml DMSO and mixed with the succinoylated-phytoglycogen solution. The mixture was cooled to 0° C. and 0.2 g EDAC (N-(3-Dimethylaminopropyl)-N'-ethylcarbodiimide hydrochloride), dissolved in milliQ water, was added to it with vigorous stirring. The reaction was allowed to proceed at RT for 24h, and then the sample was precipitated with one volume of ethanol. The precipitate was re-suspended in water and the precipitation step was repeated two more times. After the last precipitation step the sample was taken up in water and was lyophilized.

The succinoylated-phytoglycogen was prepared as follows:

4 g phytoglycogen was dissolved in 34 ml DMSO and 0.3 g DMAP (4-Dimethylaminopyridine) and 0.4 g Succinic anhydride were given to the solution. The sample was incubated (with stirring) 0/N at 50° C. After the incubation 50 ml of distilled water was added to the reaction mixture and the pH was adjusted to 7. The sample was precipitated with 1 volume of ethanol. After centrifugation the pellet was dispersed in dist. water (75 ml) the pH was adjusted to 7.0-7.2. The precipitation step was repeated twice and the sample was air dried 0/N on RT then at 60° C. for two days.

EXAMPLE 14

Photostability of Phytoglycogen-ethyl-4-Aminocinnamate Conjugate Versus Aminocinnamate Aminocinnamate and a phytoglycogen-ethyl-4-aminocinnamate conjugate were dissolved in ethanol or in water, respectively.

Solutions were deposited as thin films onto a quartz plate and dried in air for 30 min. After drying, the samples were irradiated with UV light, as in Example 11, for 4 h and then tested for their photostability.

Photodegradation was calculated from the decrease in the maximum absorption of the respective products. The results are shown in FIG. 7.

It can be seen from the data shown in FIG. 7 that the phytoglycogen-ethyl-4-aminocinnamate conjugate retained 95% of its activity after 4 h of exposure to the UV-irradiation, compared to 40% of its activity for the aminocinnamate.

EXAMPLE 15

Relative water retention versus time was compared for a polyfunctional additive prepared according to Example 1, glycerin, PEG 400 and hyaluronic acid. Samples were allowed to absorb water in a moisture chamber for ten days at 37° C. After quantifying the water uptake, the samples were placed in a closed chamber with desiccant and the time dependence on their relative water content was measured for ten days. The results are shown in FIG. 8, with each data point representing the average of three independent measurements.

EXAMPLE 16

Tolerance of Phytoglycogen Viscosity to Ionic Strength

Aqueous dispersions of 20% (w/w) phytoglycogen (prepared according to Example 1) were used for rheology tests.

The measurements were performed on a RA 2000 Rheometer (TA Instruments-Waters LLC), using a cone-plate geometry (4 cm dia plate, 1.58° steel cone; truncation gap=50.8 μm). The tests were run at 20° C. Results are shown in FIG. 9.

EXAMPLE 17

The toxicity of a monodisperse glycogen additive isolated from shellfish was tested on Hep2 cell line and compared to that of PLGA nanoparticles that are commonly used in drug delivery systems (FIGS. 10 and 11). In the experiments, the number of dead cells (FIG. 10) and release of LDH (lactate dehydrogenase) (FIG. 11) showed no noticeable toxicity for the polyfunctional additive of Example 1 at concentrations that were an order of magnitude higher than are known to be toxic for PGLA.

What is claimed is:

1. A method for changing the rheological behavior of a water-based or alcohol-based formulation comprising adding a composition of monodisperse phytoglycogen nanoparticles to the formulation wherein the composition has a polydispersity index of less than about 0.3 as measured by dynamic light scattering, wherein the change in rheological behavior comprises imparting thixotropic behavior or wherein the formulation is thixotropic and the change in rheological behavior comprises an increase in rebuilding time; wherein the monodisperse phytoglycogen nanoparticles comprises about 2.2% to about 15% w/w of the formulation.

2. The method of claim 1, wherein the formulation is a dispersion or solution of at least one small molecule, polymer, biopolymer, colloidal particle or an oil.

3. The method of claim 2, wherein the formulation is a water-based formulation.

4. The method of claim 2, wherein the formulation is an alcohol-based formulation.

5. The method of claim 4, wherein the alcohol is ethyl alcohol, propyl alcohol, isopropyl alcohol, ethylene glycol, propylene glycol, butylene glycol, dipropylene glycol, ethoxydiglycol, glycerol or a combination thereof.

6. The method of claim 1, wherein at least about 80% by dry weight of the composition is monodisperse phytoglycogen nanoparticles having an average particle diameter of between about 30 nm and about 150 nm.

7. The method of claim 1, wherein the monodisperse phytoglycogen nanoparticles are chemically modified.

8. The method of claim 7, wherein the monodisperse phytoglycogen nanoparticles are modified by chemical functionalization of at least one of its hydroxyl groups with a carbonyl group, an amine group, a thiol group, a carboxylic group, or a hydrocarbyl.

9. The method of claim 8 wherein the hydrocarbyl group is an alkyl, vinyl or allyl group.

10. The method of claim 7, wherein the monodisperse glycogen or phytoglycogen nanoparticle is modified with octenyl succinic acid.

11. The method claim 1, wherein the formulation comprises a natural gum.

12. The method of claim 1 wherein the formulation is a food, a cosmetic, a personal care product, a nutraceutical, a pharmaceutical, a lotion, a gel, a paint, a coating, an ink, a lubricant, an excipient, a surface film, a stabilizer or a drilling mud.

13. The method of claim 1, wherein the monodisperse phytoglycogen nanoparticles comprises about 10 to about 15 % w/w of the formulation.

14. The method of claim 1, wherein the monodisperse phytoglycogen nanoparticles comprise about 5 to about 15% w/w of the formulation.

15. A method for changing the rheological behavior of a water-based or alcohol-based formulation comprising adding a composition of monodisperse phytoglycogen nanoparticies to the formulation wherein the composition has a polydispersity index of less than about 0.3 as measured by dynamic light scattering, wherein the change in rheological behavior comprises imparting thixotropic behavior or wherein the formulation is thixotropic and the change in relogical behavior comprises an increase in rebuilding time; wherein the monodisperse phytoglycogen nanoparticles comprisies about 5% to about 25% w/w of the formulation.

* * * * *